US010801022B2

(12) United States Patent
Li et al.

(10) Patent No.: US 10,801,022 B2
(45) Date of Patent: Oct. 13, 2020

(54) METHOD FOR SOLID-PHASE SYNTHESIS OF DNA ENCODED COMPOUND LIBRARY

(71) Applicant: HITGEN LTD, Chengdu (CN)

(72) Inventors: Jin Li, Chengdu (CN); Jinqiao Wan, Chengdu (CN); Guansai Liu, Chengdu (CN); Dengfeng Dou, Chengdu (CN)

(73) Assignee: Hitgen INC., Chengdu (CN)

( * ) Notice: Subject to any disclaimer, the term of this patent is extended or adjusted under 35 U.S.C. 154(b) by 140 days.

(21) Appl. No.: 15/782,914

(22) Filed: Oct. 13, 2017

(65) Prior Publication Data

US 2018/0155710 A1    Jun. 7, 2018

Related U.S. Application Data

(63) Continuation of application No. PCT/CN2016/079171, filed on Apr. 13, 2016.

(30) Foreign Application Priority Data

Apr. 14, 2015 (CN) .......................... 2015 1 0176488

(51) Int. Cl.
| | | |
|---|---|---|
| *C12N 15/10* | (2006.01) | |
| *C40B 50/00* | (2006.01) | |
| *C40B 70/00* | (2006.01) | |
| *C40B 40/06* | (2006.01) | |
| *C40B 50/04* | (2006.01) | |
| *C40B 50/16* | (2006.01) | |
| *C40B 20/04* | (2006.01) | |
| *C12P 19/34* | (2006.01) | |

(52) U.S. Cl.
CPC .......... *C12N 15/1068* (2013.01); *C12P 19/34* (2013.01); *C40B 20/04* (2013.01); *C40B 40/06* (2013.01); *C40B 50/04* (2013.01); *C40B 50/16* (2013.01); *C40B 70/00* (2013.01)

(58) Field of Classification Search
CPC ..................................................... C12N 15/10
See application file for complete search history.

(56) References Cited

U.S. PATENT DOCUMENTS

| | | | | |
|---|---|---|---|---|
| 2004/0180412 A1* | 9/2004 | Liu | .................... | C12N 15/1068 506/1 |
| 2011/0136697 A1* | 6/2011 | Morgan | ................. | C07H 21/00 506/26 |
| 2015/0211002 A1* | 7/2015 | Keefe | ................ | C12N 15/1044 506/2 |
| 2018/0155710 A1* | 6/2018 | Li | ........................... | C40B 20/04 |
| 2018/0245241 A1* | 8/2018 | Berlin | .............. | G01N 33/54346 |

FOREIGN PATENT DOCUMENTS

| | | |
|---|---|---|
| CN | 102317513 A | 1/2012 |
| CN | 103882532 A | 6/2014 |
| WO | 2005058479 A2 | 6/2005 |

OTHER PUBLICATIONS

Li et al., Design, Preparation, and Selection of DNA-Encoded Dynamic Libraries, Chemical Science, 2015, 6, 7097-7104. (Year: 2015).*
Leimbacher et al., Discovery of Small-Molecule Interleukin-2 Inhibitors From a DNA-Encoded Chemical Library, Chemistry European Journal, 2012, 18, 7729-7737. (Year: 2012).*
Li et al., Multistep DNA-Templated Synthesis Using a Universal Template, Journal of the American Chemical Society, 2013, 135, 17727-17730. (Year: 2013).*

* cited by examiner

*Primary Examiner* — Amy M Bunker
(74) *Attorney, Agent, or Firm* — Wayne & Ken, LLC; Tony Hom

(57) ABSTRACT

The present invention provides a method of solid-phase synthesis of DNA-encoded compound library. The method includes following steps: a) reacting solid carrier G-1 with linker molecule L-1 to prepare L-G-1; b) reacting DNA with linker molecule L-0 to prepare L-2; c) reacting L-G-1 with L-2 to prepare L-G-2; d) removing protection group of the L-G-2 and obtaining L-G-2-1; e) reacting the L-G-2-1 with synthetic building block and performing DNA encoding; and f) removing the solid carrier and obtaining the DNA-encoded compound library. Compared with the prior art, the present invention can complete post-treatment purification of the reaction only by filtration and irrigation processes for several times. The present invention is simple to operate, can shorten the production cycle of DNA encoded compound library with more than 50%, significantly increases the production efficiency and the unicity as well as the purity of the final products.

15 Claims, No Drawings

Specification includes a Sequence Listing.

METHOD FOR SOLID-PHASE SYNTHESIS OF DNA ENCODED COMPOUND LIBRARY

REFERENCE TO AN ELECTRONIC SEQUENCE LISTING

The contents of the electronic sequence listing (15782914SeqList1.txt; Size: 2,000 bytes: and Date of Creation: Feb. 12, 2018) is herein incorporated by reference in its entirety.

TECHNICAL FIELD

The present invention relates to a method for solid-phase synthesis of DNA encoded compound library.

BACKGROUND

High throughput screening (HTS) aiming at biological targets is one of the major means to rapidly obtain lead compounds in research and development of pharmaceuticals. However, this method imposes a restriction on efficiency and possibility of discovering lead compounds, given to a long time needed for traditional HTS of a single molecule, enoumous investment of equipments, a limited amount of library compounds (counted in millions) as well as over-long establishment of compound library in terms of several decades. DNA encoded compound library found in recent years combine combinatorial chemistry and molecular biology and is able to synthesis a compound library with up to hundreds of million molecules within a very short time by adding a DNA tag to every compound at a molecular level. Also, these compounds can be identified by gene sequencing. It largely increase size of a compound library as well as synthesis efficiency and becomes a trend of the next generation of compound library screening technology. A extensive application in pharmaceutical industry has already started in developed countries, producing a great number of positive results (Accounts of Chemical Research, 2014, 47, 1247-1255).

Since every compound molecule in the DNA encoded compound library has a special given DNA sequence, the screening of a compound library is able to take the DNA encoded compound library which contains ten million or even hundred million of compounds as a whole, dissolving them into tens of micro liters to perform the high throughput screening of biological targets under normal laboratory conditions. No screening equipments are necessary and complex management system for compounds library is avoided compared to the traditional high throughput screening, which enormously saves equipment investment as well as screening cost.

In 1993, inspired by genetic DNA tag, Brenner et al utilized the encoding of beads, making every bead attached to a single compound and encoding the synthesis process into the beads, and identified compounds which attached to the bead by reading the code on the bead. This solid-phase "method for synthesis of DNA encoded combinatorial chemistry" was presented in the American chemistry society (J. Am. Chem. Soc. 1993, 115, 9812-9813). However, the method Brenner presented can only be applied on the synthesis of polypeptide library, the need for synthesis of small molecule compound library in the modern chemistry and pharmaceutical industries is still not meet.

Later on, Pehr B. Harbury et al., has developed another method for solid-phase synthesis of DNA encoded compound library and utilized it on the synthesis of polypeptide (PloS Biology year 2004, 2, page 1031-1038). But the solid applied is the anion exchange resin DEAE sepharose. The forces between solid carrier and DNA mainly come from ion-ion interaction. There is thus hardly stable existence in high-salute system or in the system where other influencing ions interact, which impose a large restriction on the application of synthesis of small compound library.

An invention application numbered CN201210555548.3, namely "Synthesis and Screening Method and Kit for Lead Compound", disclose a technology in synthesis and encoding of a DNA encoded compound library. It comprises steps as follows. Firstly the beginning sequence of a single strand in DNA is connected with the synthetic building block, and the other end of the strand is series connected with special marker of the synthesis building block in order to derive a begin synthetic building block whose end marked with a single strand DNA; then based on the begin synthetic building block, compounds are synthesized by using linear combination reactions. In the process of synthesis, each time a new synthesis building block is added, a special maker sequence of the new block is series connected with the free-end of single strand DNA which connected to the begin synthesis buiding block, increasing length of the described the single strand DNA; finally the free-end of single strand DNA is connected to the end sequence and a single strand DNA encoded compound library is derived. This invention, combined with screening and sequencing processes, is able to synthesize target lead compound rapidly and efficiently.

The existing technology in synthesis and encoding of DNA encoded compound library has some drawbacks and limitations, although it can be well applied on the screening of lead compounds. Above all, the encoded DNA, to a large degree, is only available in an aqueous (or an aqueous phase containing an organic solvent which is dissolved in water) reaction. Solubility of reacting molecules in pure organic solvents is poor so that this method can not be applied to the reaction with water-sensitive pure organic solvents, thus limiting type of synthesis applying DNA encoded compound library and decreasing the synthesis rate of DNA encoded compound library. Secondly, an over-dose of small molecule reactant is often used in order to encourage each reaction step to react entirely but it is hard to separate the reactants completely from water-based DNA encoded compound library. Finally, the separation and purification processes always contains complex procedures and always take a long cycle to make sure that purification requirement of DNA compound library is meet after the DNA library synthesis during which is based on liquid reaction.

Nowadays, the present solid-based method for DNA encoded compound synthesis which is only applied on synthesis of polypeptides covers a limited type of chemical reactions. Moreover, the forces between solid carrier and DNA mainly come from ion-ion interaction. There is thus hardly stable existence in high-salute system or in the system where other influencing ions interact, which impose a large restriction on the application of synthesis of small compound library.

In all, a new method for solid-phase synthesis of DNA encoded compound library is needed, with easy procedures, a low cost, a short cycle and an organic solvent suitable system.

SUMMARY

The present invention disclose a method for solid-phase synthesis of DNA encoded compound library, in order to solve the above mentioned problems. It optimizes the method for synthesis and purification processes of DNA encoded compound library, increases the structural diversity of small chemical molecules in DNA encoded compound library, and enlarges the scope of its application on screening of new pharmaceuticals.

Terminologies appearing in the following description are explained as follows.

Synthetic Building Block, namely synthon, refers to a kind of small molecules used in the research and development of new pharmaceuticals (Western medicine and traditional Chinese medicine) which has a variety of physical properties as well as specific chemical properties.

Solid carrier, refers to a solid material for carrying other molecules used in a solid-phase reaction.

Linker molecule, also namely as binding molecule, refers to a kind of compound having a special group to connect DNA, small molecule compound library and solid carrier together.

CPG (Controlled pore Glass) refers to micro-pore glass balls made from silicon dioxide. It has a large number of random pores inside the balls with the pores forming a large network. The size of the pore is named pore diameter, the pore diameter is very stable.

The present invention provides a method for solid-phase synthesis of a DNA-encoded compound library, the method comprises the following steps:

g. reacting a solid carrier G-1 with a linker molecule L-1, separating, purifying and obtaining L-G-1;

h. reacting DNA with a linker molecule L-0, separating, purifying and obtaining L-2;

i. reacting the L-G-1 with the L-2, separating, purifying and obtaining L-G-2;

j. removing a protection group of the L-G-2 and obtaining L-G-2-1; and k. adopting method 1, method 2, method 3, method 4 or any combination thereof:

method 1, comprising:

reacting the L-G-2-1 with $R^1$, separating, purifying and obtaining L-G-2-1-1;

performing DNA encoding on the L-G-2-1-1 and obtaining L-G-3-1;

or method 2, comprising:

iii. reacting the L-G-2-1 with skeleton molecules, separating, purifying and obtaining L-G-2-2; and iv. reacting the L-G-2-2 with $R^1$ or reacting the $R^1$ with the L-G-2-2 having protection group removed, separating, purifying and obtaining L-G-2-2-1; performing DNA encoding on the L-G-2-2-1 and obtaining L-G-3-1;

or method 3, comprising:

iv. reacting the L-G-2-1 with skeleton molecules, separating, purifying and obtaining L-G-2-2;

v. reacting the $R^1$ with the L-G-2-2 or reacting the $R^1$ with the L-G-2-2 having protection group removed, searating, purifying and obtaining L-G-2-2-1; performing DNA encoding on the L-G-2-2-1 and obtaining L-G-3-1; and vi. reacting a $R^2$ with the L-G-3-1 or reacting the $R^2$ with the L-G-3-1 having protection group removed, separating, purifying and obtaining L-G-3-1-1; performing DNA encoding on the L-G-3-1-1 and obtaining L-G-3-2;

or method 4, comprising:

iii. Reacting L-G-2-1 with skeleton molecules, separating, purifying and obtaining L-G-2-2; performing DNA encoding on the L-G-2-2 and obtaining L-G-3-1;

iv. reacting the R2 with the L-G-3-1 or reacting the R2 with the L-G-3-1 having protection group removed, separating, purifying and obtaining L-G-3-1-1; performing DNA encoding on the L-G-3-1-1 and obtaining L-G-3-2;

wherein, $R^1$ and $R^2$ are synthetic building blocks;

I. removing the solid carrier from L-G-3-1, L-G-3-1 and/or L-G-3-2 and obtaining DNA-encoded compound library L-D-T.

Further, in step a, the described solid carrier is selected from any one or more of a PEG resin, a PEGA resin, an inorganic carrier and a PE thin plate.

Further, in step a, the described solid carrier is from a solid carrier containing amino active functional group, preferably the solid carrier is controlled pore glass (CPG) beads comprising a free amine.

Further, in step a, the described linker molecule L-1 is selected from a compound containing any one or more of functional groups consisting of ester group, sulfur-ester group, ortho-nitrobenzyl group, coumarin group, aromatic ketone groups, nitrine, hydroxyl group, sulfhydryl group, thioether group, carboxyl group, aldehyde group, amino groups, amide group, alkenyl group and alkynyl group; and the described linker molecule L-1 is

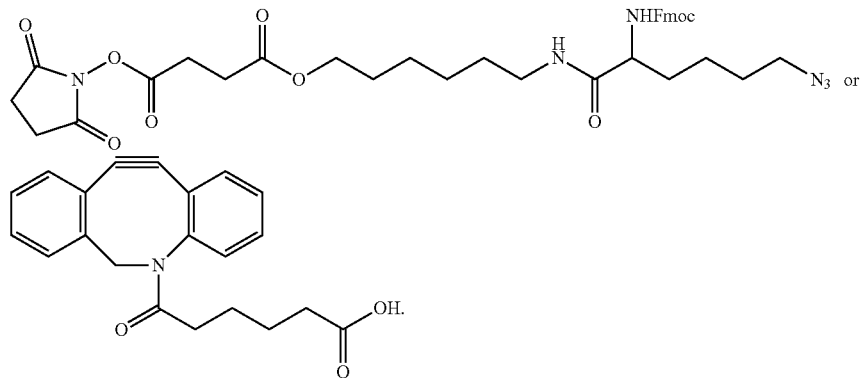

Further, in step a, a weight ratio of the described solid carrier G-1 and the described linker molecule L-1 is 1:(0.08~0.2); preferably, a weight ratio of the described solid carrier G-1 and the described linker molecule L-1 is 1:0.138.

Further, in step a, the reaction solvent is a halogenated hydrocarbon solvent; preferably, reaction solvent is dichloromethane.

Further, in step a, the reaction temperature is 15-25° C. and reaction time is 12-16 hours.

Further, in step a, the method of separation and purification is removing a solvent to obtain a solid and washing the solid by DMF and dichloromethane.

Further, in step a, the described L-G-1 is

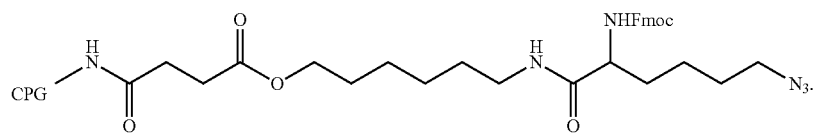

Further, in step b, the described DNA is single-strand DNA.

Further, in step b, the described linker molecule L-0 is selected from a compound containing any one or more of functional groups consisting of ester group, sulfur-ester group, ortho-nitrobenzyl group, coumarin group, aromatic ketone groups, nitrine, hydroxyl group, sulfhydryl group, thioether group, carboxyl group, aldehyde group, amino groups, amide group, alkenyl group and alkynyl group; preferably, the described linker molecule is

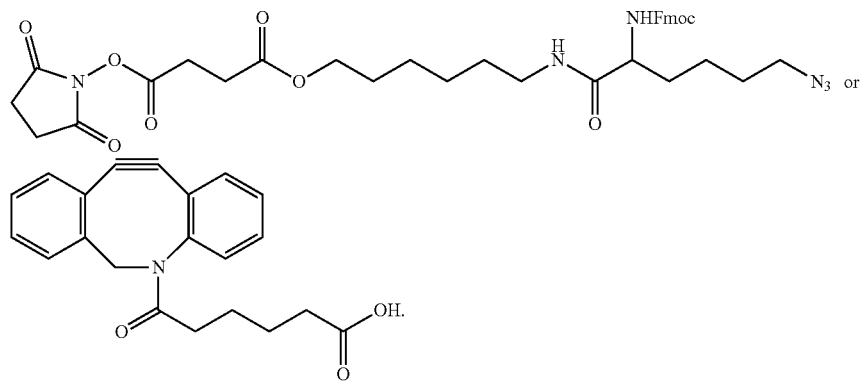

Further, in step b, reaction is carried out with a condensing agent.

Further, in step b, the condensing agent is 2-Chloro-4,6-dimethoxy-1,3,5-triazine.

Further, in step b, the molar ratio of DNA and the linker molecule L-0 is 1:50~300 and the molar ratio of the linker molecule L-0 and the condensing agent is 1:1~2; preferably, the molar ratio of DNA and the linker molecule L-0 is 1:100 and the molar ratio of the linker molecule L-0 and the condensing agent is 1:1.

Further, in step b, the reaction temperature is 15~25° C. and reaction time is 12~16 hours.

Further, in step b, the method of separation and purification comprises: adjusting pH to 4~5, adding ethanol, precipitating at −20° C., washing and obtaining a solid.

Further, in step b, the L-2 is:

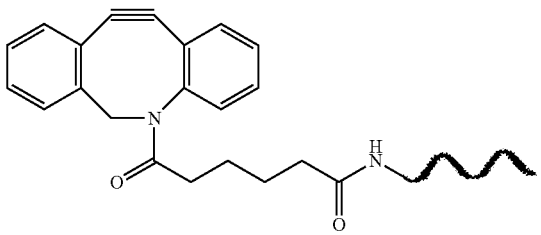 [SMILES: CNC(=O)CCCCC(=O)N1Cc2ccccc2C#Cc2ccccc21]

wherein ∿∿ is DNA.

Further, in step c, the reaction is carried out with an organic solvent; and a reaction solvent is pyridine.

Further, in step c, a molar ratio of L-G-1 and L-2 is 2~10:1 and the weigh-to-volume ratio of L-G-1 and the pyridine is 1:1 mg/L.

Further, in step c, the reaction temperature is 20~45° C., and reaction time is 14~30 hours; preferably, the reaction temperature is 40° C. and the reaction time is 21 hours.

Further, in step c, the method of separation and purification is: removing the solvent to derive solids and washing solids with water and TEAA buffer solution.

Further, in step c, the described L-G-2 is

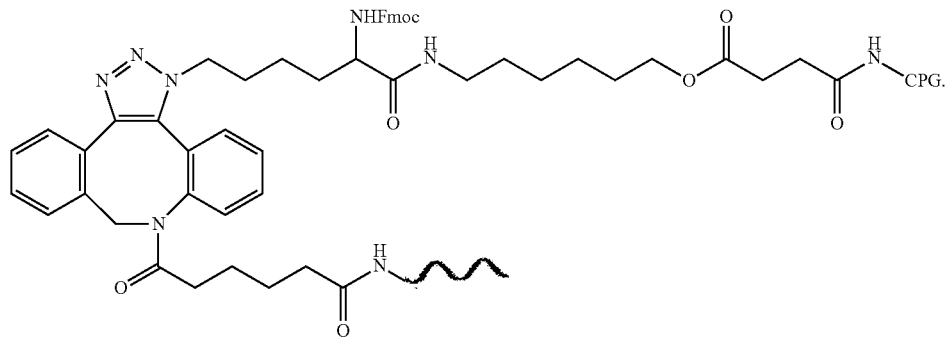

Further, in step d, the protection group is amino protection group, preferably, the protection group is Fluorenyl-methoxycarbonyl group (FMOC).

Further, in step d, the protection group is removed of L-G-2 with piperidine and nitrogen-containing solvent, wherein a molar volume ratio of the described L-G-2 and piperidine is 1:(100~10000) mol/L and a volume ratio of the piperidine and the nitrogen-containing solvent is (1~4):(5~20).

Further, in step d, the described L-G-2-1 is

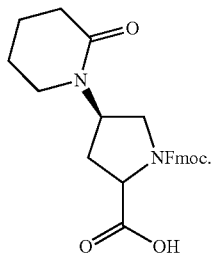

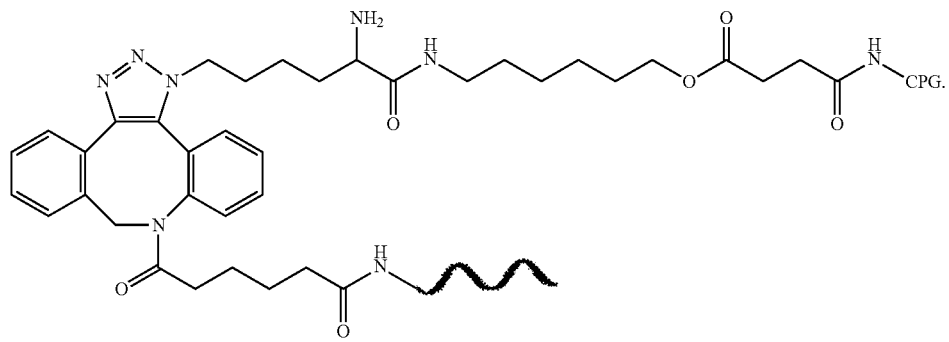

Further, in step e, the method of DNA encoding comprises: connecting marker sequence i with DNA of L-G-2-1-1, L-G-2-2-1, L-G-3-1-1 or L-G-2-2 in series and marking $R^i$ specifically with the marker sequence i; wherein $R^i$ is a synthetic building block, i=1 or 2; connecting the marker sequence i on DNA or marker sequence (i-1) in series when a new $R^i$ is added each time during the synthesis; and connecting a terminal sequence on the marker sequence i after the synthesis is completed.

Further, in step e, the described $R^1$ and $R^2$ are respectively or simultaneously selected from polyfunctional group compounds, and the polyfunctional groups are independently selected from any two or more of groups consisting of amino, carboxyl, aldehyde group, alkenyl, alkynyl, halogen, azide group, hydroxyl group, sulfhydryl group and phenyl group; preferably, the described $R^1$ and $R^2$ are respectively or simultaneously selected from amino acid, substituted or unsubstituted carboxylic acids, substituted or unsubstituted amines, substituted or unsubstituted alkenes, substituted or unsubstituted alkynes, substituted or unsubstituted aldehydes, isocyanate; and the described $R^1$ and $R^2$ are respectively or simultaneously selected from isocyanate, benzyl alcohol or benzoic acid.

Further, in step e, the described skeleton molecules contain any one or more of groups consisting of hydroxyl group, amino group, carboxyl group, cyanate group and aldehyde group.

Further, in step e, the described skeleton molecules are selected from any one or more of molecules consisting of 3-(4-hydroxyphenyl)propionic acid, 4-aminobenzoic acid, dl-4-hydroxyphenylglycine, FMOC-glycine, FMOC-1-phenylalanine, t-butylisocynide, cyclohexyl isocyanide, 3-methyl butyraldehyde, cyclopentyl aldehyde and Further, the reaction is carried out under the condition of an organic amine and an organic solvent; preferably, the reaction is carried out under the condition of triethylamine and dimethylformamide.

Further, in method 1 of step e, a molar ratio of L-G-2-1, $R^1$ and the organic amine is 1:(50~500):(50~500), a molar volume ratio of L-G-2-1 and the organic solvent is 1:(50~500) nmol/μL; and the molar ratio of L-G-2-1, $R^1$ and the organic amine is 1:150:150 and the molar volume ratio of L-G-2-1 and the organic solvent is 1:240 nmol/μL.

Further, in method 1 of step e, the reaction temperature is 25° C.~30° C. and the reaction time is 12~16 hours.

Further, in method 1 of step e, the method of separation and purification is: removing the solvent to derive solids, washing solids with water and TEAA buffer solution.

Further, in method 2 or method 3 of step e, the reaction in the step i is carried out under the condition of a condensing agent, an organic amine and an organic solvent; in the method 4 of the step e, the reaction in the step i is carried out under the condition of organic solvent; and the reaction is carried out under the condition of 2-(7-azobenzene and -triazole)-N,N,N',N'-tetramethylurea hexafluorophosphate, N,N-ethyldiisopropylamine and the nitrogen containing solvent;

a molar ratio of the described L-G-2-1, the skeleton molecule, the condensing agent and the organic amine is 1:50~500:50~500:50~500: a molar volume ratio of the described compounds L-G-2-1 and the nitrogen solvent is 50~500 nmol/μL.

Further, in method 2, method 3 or method 4 of step e, the reaction temperature in step i is 25° C.~30° C. and reaction time is 12~16 hours.

Further, in method 2, method 3 or method 4 of step e, the method of separation and purification in step i is: removing the solvent to derive solids, washing solids with water and TEAA buffer solution.

Further, in method 2, method 3 or method 4 of step e, the reaction in the step ii is carried out under the condition of an organic amine or organic phosphine and an organic solvent; and the described organic amine is selected from N,N-ethyldiisopropylamine or triethylamine, the described organic phosphine is triphenylphosphine and the described organic solvent is selected from halohydrocarbon solvents, ethers solvents and nitrogen solvents; and the described ethers solvent is tetrahydrofuran and the nitrogen solvent is N,N-dimethylformamide.

Further, in method 2, method 3 or method 4 of step e, the reaction temperature in step ii is 25° C.~30° C. and reaction time is 12~16 hours.

Further, in method 2, method 3 or method 4 of step e, the method of separation and purification in the step ii is: removing the solvent to obtain a solid, washing the solid with water and TEAA buffer solution.

Further, in method 2, method 3 or method 4 of step e, the method of removing the protection group from L-G-2-2 or L-G-3-1 is: adding piperidine into L-G-2-2 or L-G-3-1, stirring at 25° C.~30° C. for 2~6 hours, removing the solvent to obtain a solid, and washing the solid with water and TEAA buffer solution.

Further, in method 3 or method 4 of step e, the reaction with $R^2$ is carried out under the condition of organic amines and organic solvents; and the described organic amine is selected from N,N-ethyldiisopropylamine or triethylamine, and the described organic solvent is selected from halohydrocarbon solvents.

Further, in method 3 or method 4 of step e, the temperature of reaction with $R^2$ is 25° C.~30° C. and the time of reaction with $R^2$ is 12~16 hours.

Further, in method 2, method 3 or method 4 of step e, the method of separation and purification in step iii is: removing the solvent to obtain a solid, and washing the solid with water and TEAA buffer solution.

Further, in step e, the described L-G-3-1 is

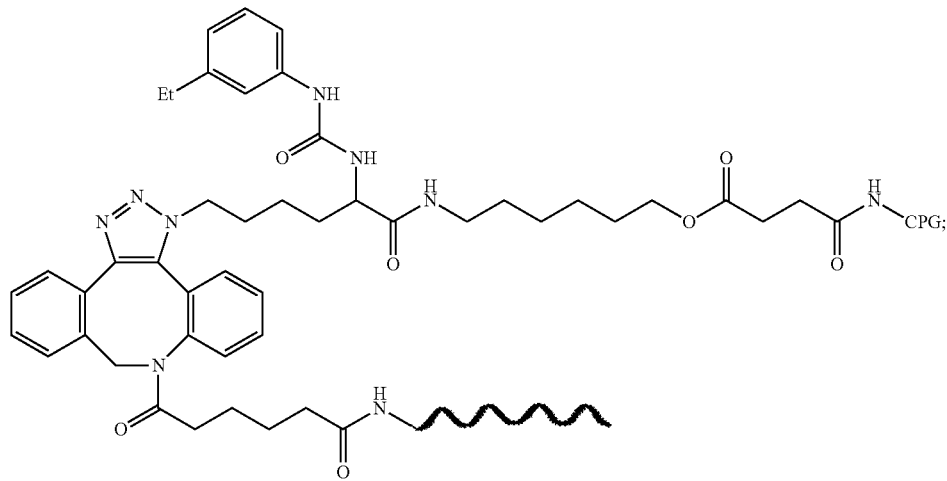

the described L-G-2-2 is

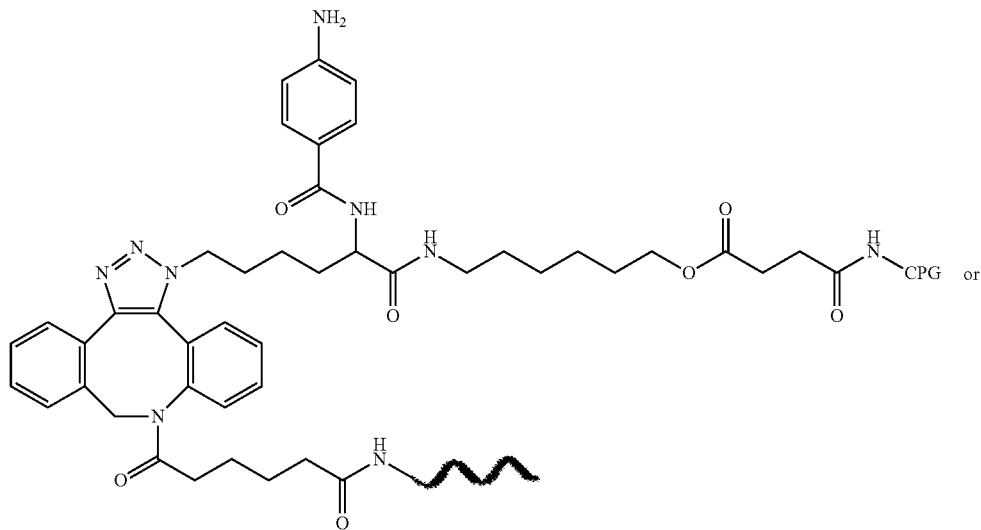

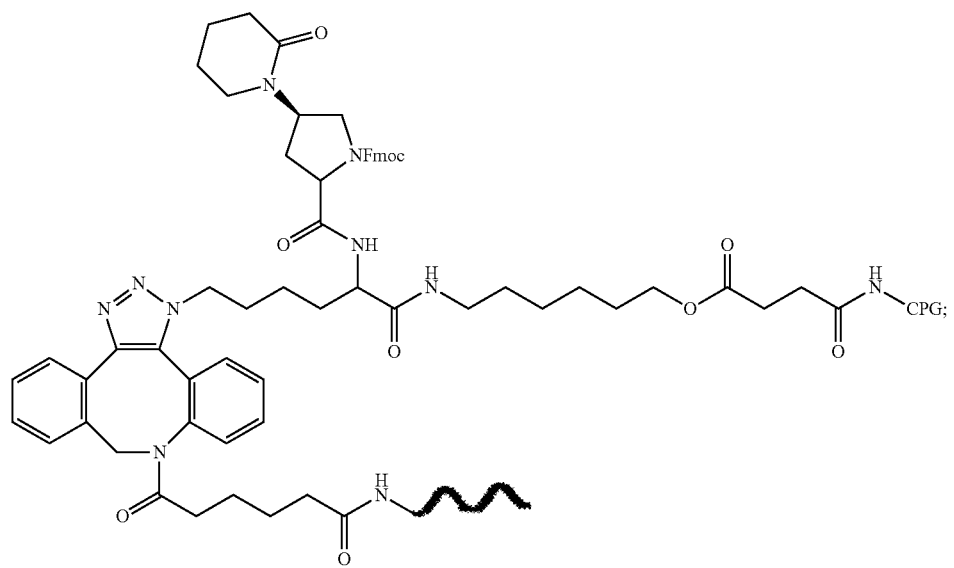
the described is L-G-3-1 is:
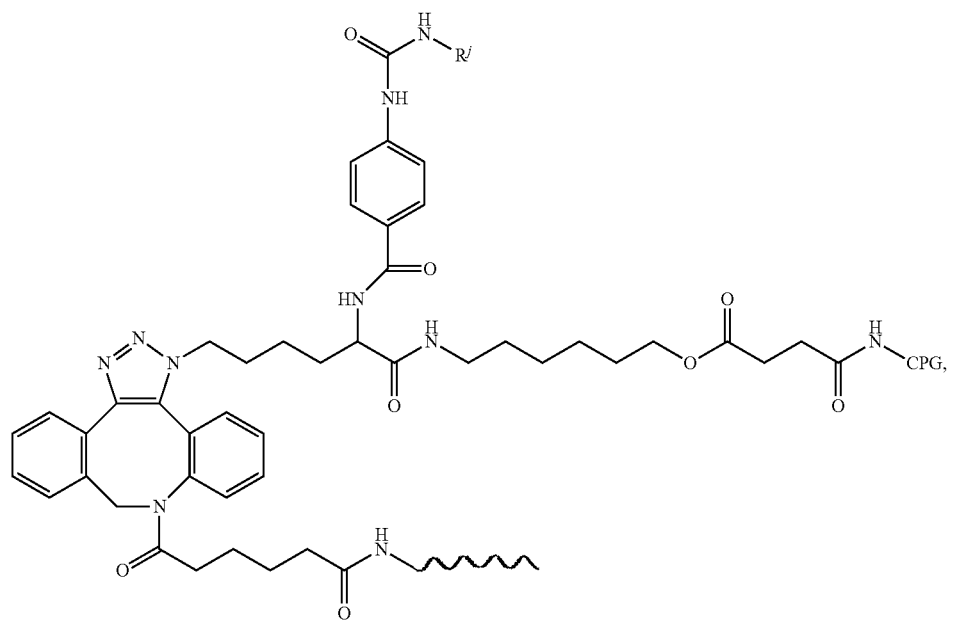

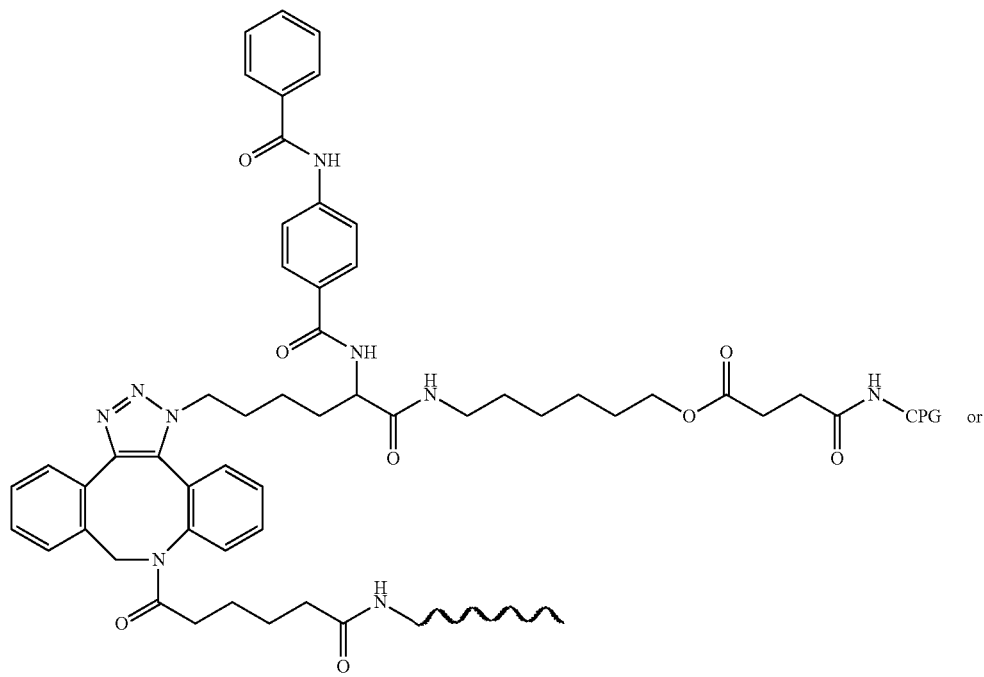

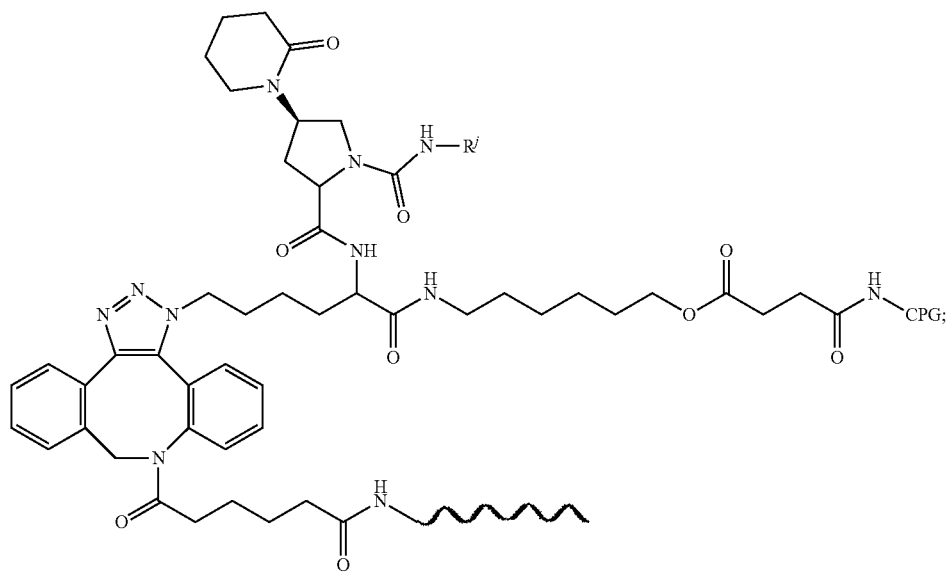

wherein, $R^j$ is a group able to form isocyanate.

Further, in step f, the method of removing the solid carrier comprises:

ii. taking L-G-3-1, L-G-3-1 and/or L-G-3-2, adding an alkaline for reaction, separating and purifying; or iii. taking L-G-3-1, L-G-3-1 and/or L-G-3-2, adding PBS buffer solution, performing decomposition reaction under light source, separating and purifying.

Further, in step i. the described alkaline is an inorganic alkaline; reaction temperature is 30° C.~60° C.; reaction time is 1~10 hours; preferably, the described alkaline is aqueous ammonia; reaction temperature is 55° C.; reaction time is 1 hour.

Further, in step ii, the wavelength of the light is 365 nm; temperature of the decomposition reaction is 25° C.~40° C.; the reaction time is 1~8 hours.

Further, in step i and/or step ii,
the method of separation and purification is: washing with water and TEAA buffer solution to obtain a filtrate; adding ethanol after concentrating the filtrate, precipitating at −20° C., centrifugating, obtaining a solid and washing the solid.

15

Further, in step f, the described L-D-T is

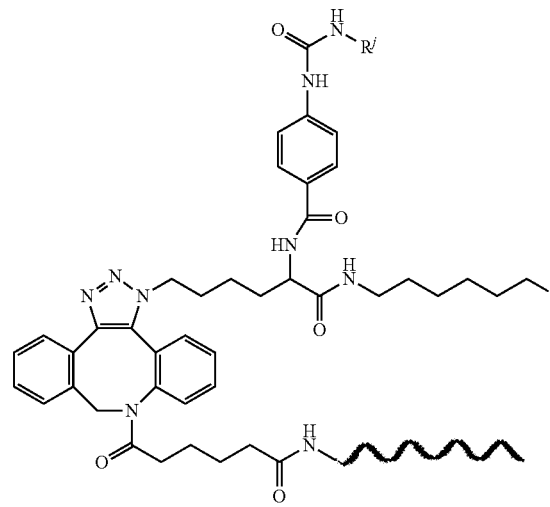

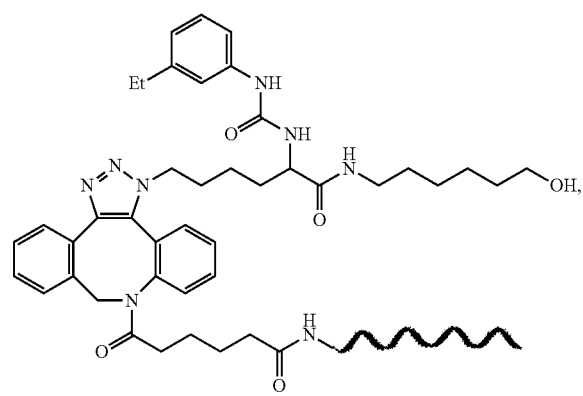

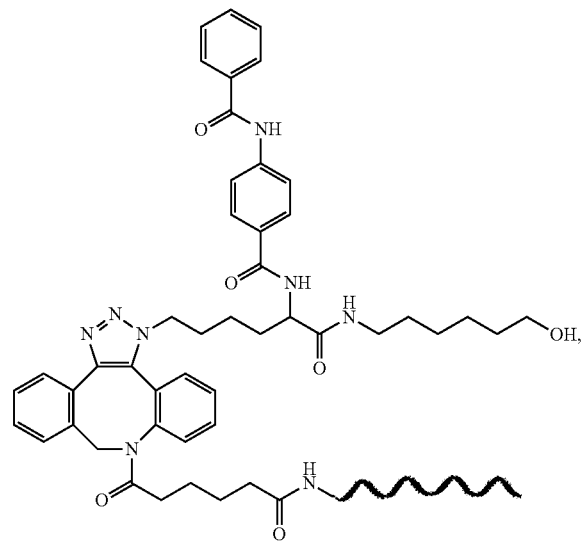

16
-continued

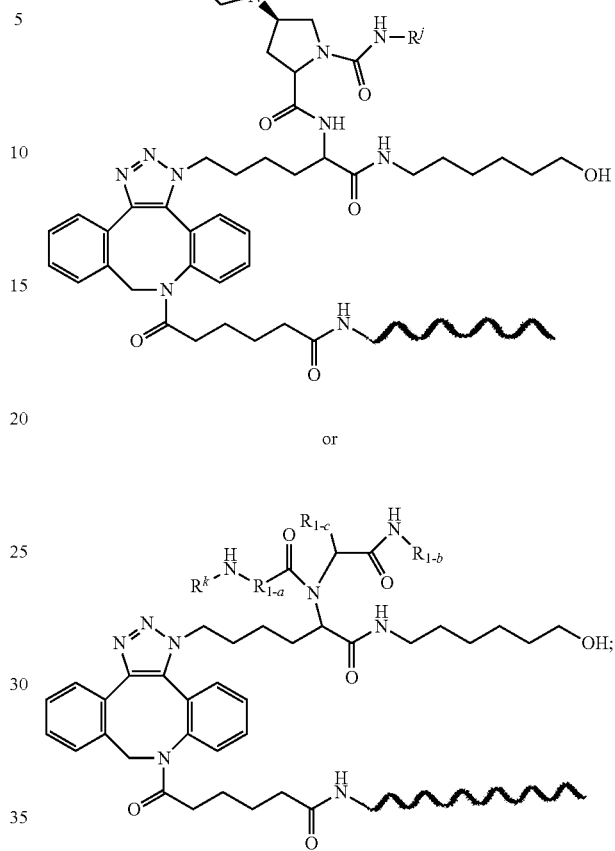

wherein, $R^1$ is a group able to form isocyanate; $R_{1-a}$ is —$CH_2$— or —$C_6H_5CH_2CH$—; $R_{1-b}$ is n-butyl, isobutyl, tertiary butyl or cyclohexyl; $R_{1-c}$ is n-propyl, isopropyl or cyclopentyl; $R^k$ is a group produced by amino group reacting with any one of carboxylic acid, aldehyde and isocyanate.

The present invention provides a kind of DNA encoded compound library, and it has general formula like formula I:

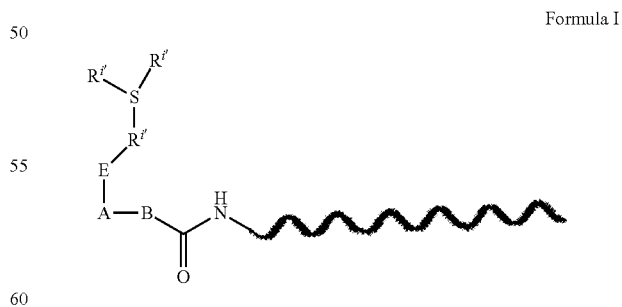

Formula I wherein,

S is a skeleton molecule in the compound library;

$R^{i'}$ is selected from hydrogen or synthetic building blocks;

E is selected from amino group, alkenyl, alkynyl, amide, ester, thioether group or azide;

A is selected from a hydroxyl group or a sulfhydryl group;
B is selected from

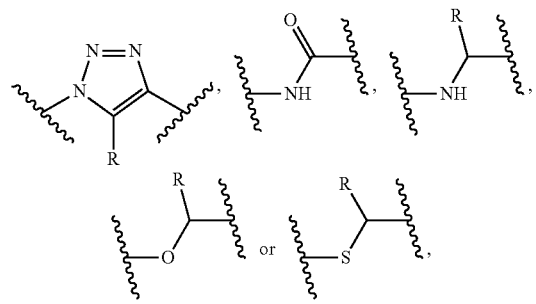

wherein R is hydrogen, C1~C8 alkyl group, C1~C8 alkenyl group or a group forming a cycle with atoms in $B_1$; $B_1$ is selected from substituted or unsubstituted alkynyl, amino, carboxyl, aldehyde, azide or sulfhydryl; and ⁓⁓ is DNA.

Further, the described skeleton molecule contains any one or more of groups consisting of hydroxyl, amino, carboxyl, cyano group and aldehyde group.

Further, the described skeleton molecule is any one or more of following molecules consisting of 3-(4-hydroxyphenyl)propionic acid, 4-aminobenzoic acid, dl-4-hydroxyphenylglycine, FMOC-glycine, FMOC-1-phenylalanine, t-butylisocynide, cyclohexyl isocyanide, 3-methyl butyraldehyde, cyclopentyl aldehyde and

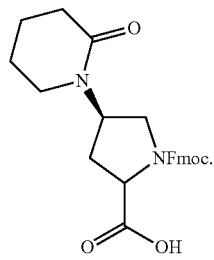

Further, molecule A has 10~50 atoms.

Further, the library contains the following DNA encoded compound library:

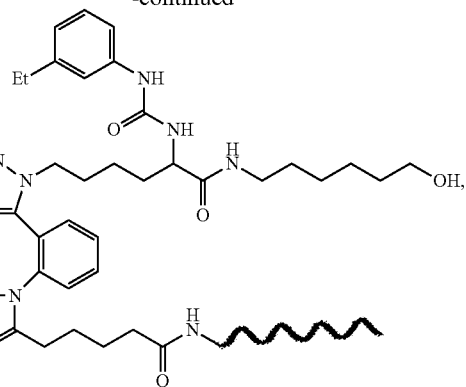

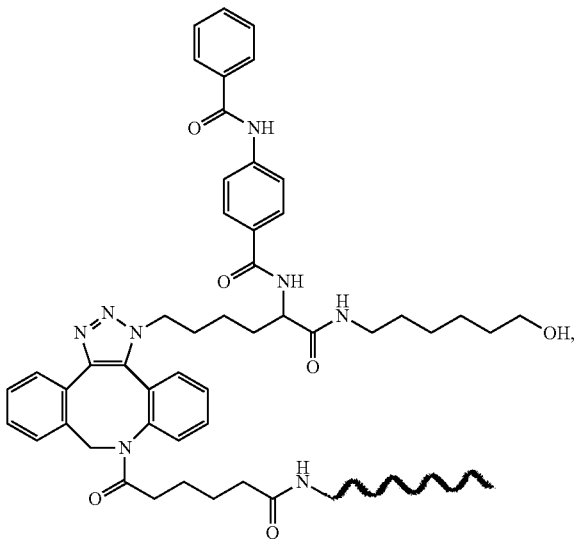

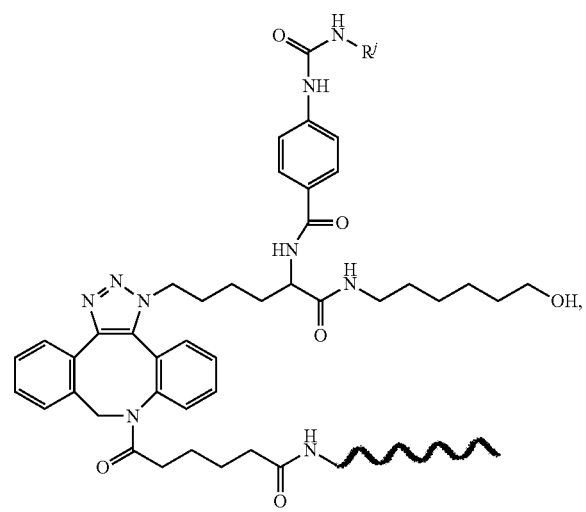

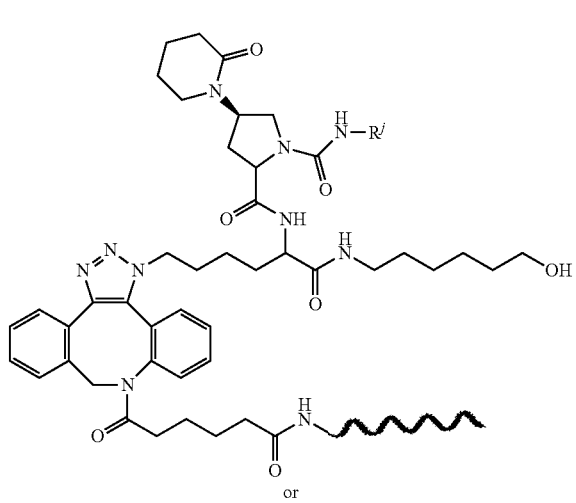

or

-continued

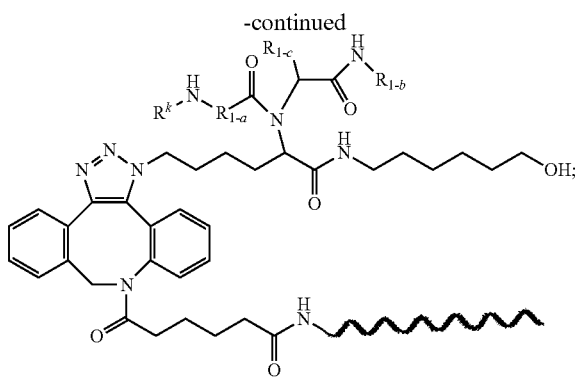

wherein, R is a group able to form isocyanate; $R_{1-a}$ is —$CH_2$— or —$C_6H_5CH_2CH$—; $R_{1-b}$ is n-butyl, isobutyl, tertiary butyl or cyclohexyl; $R_{1-c}$ is n-propyl, isopropyl or cyclopentyl; $R^k$ is a group produced by amino group reacting with any one of carboxylic acid, aldehyde and isocyanate.

Compared with the existed method for liquid phase synthesis of DNA encoded compound library, the present invention can complete post-treatment purification of the reaction only by filtration and irrigation processes for several times. The present invention is simple to operate, can shorten the production cycle of DNA encoded compound library with more than 50%, significantly increases the production efficiency and the unicity as well as the purity of the final products. Besides, the present invention has a high economic value, which is suitable for industrial application.

Specifically, technical solutions are further shown as follows.

7. Adding 3 mL of dichloromethane solution containing compound L-1 (69 mg, 0.1 mmol, from Aldrich) to G-1 (0.5 g, loading: 32 μmol/g) and allowing reaction overnight under room temperature; removing the solvent by filtration after the reaction to obtain a solid; washing the solid respectively with DMF (2 mL×3) and dichloromethane (2 mL×3) until no compound L-1 can be found in the solution with LC-MS; L-G-1 is obtained.

Taking a portion of L-G-1, removing Fmoc protection group by piperidine, determining that the loading of CPG is 14.5 μmol/g by the UV absorption of free amino groups.

8. Dissolving single strand DNA into 30 μL $NaHCO_3$ buffer solution, adding successively 20 mL of DMSO solution of L-0 (1.0 mg, 3.0 μmol, manufacturer: Aldrich) and 10 μL water solution of DMT-MM solution (0.83 mg, 3.0 μmol); allowing reaction overnight under room temperature; adjusting pH to 4~5 with 3 mol/L HCl solution after the above mentioned reaction is finished, adding 240 μL ethanol and precipitating at −20° C. for 2 hours, centrifugating to obtain a solid; washing the solid with 85% ethanol to obtain L-2.

9. Adding 90 μL aqueous solution of L-2 (28 nmol) and 10 μL pyridine into L-G-1 (10 mg, 140 nmol), and allowing reaction with stirring for 21 hours at temperate of 40° C.; filtrating the solution after the above mentioned reaction, and removing the solvent and obtain a solid; washing the solid respectively with distilled water and 0.1 mol/L TEAA buffer solution for 3 times to obtain L-G-2.

10. Adding nitrogen solvent and pyridine into L-G-2, allowing reaction with stirring for 4~6 hours at 25° C.~30° C.; filtrating the solution to remove the solvent and to get the filtrated cake; washing the filtrated cake respectively with distilled water and 0.1 mol/L TEAA buffer solution for 3 times to obtain L-G-2-1.

The molar volume ration of the described L-G-2 and pyridine is 1:(1~4) mol/mL; the volume ratio of pyridine and nitrogen-contained solvent is (1~4):(5~20).

11. Adding molecule skeleton containing carboxylic acid functional group, O-(7-azabenzotriazole-1-yl)-N,N,N',N'-trtramethyluronium hexafluorophosphate, N,N-ethyldiisopropylamine as well as halohydrocarbon derivative solvent into L-G-2-1 and allowing reaction with stirring for 12~16 hours at 25° C.~30° C.; filtrating the solution to remove the solvent to obtain a filtrated cake; washing the filtrated cake respectively with distilled water and 0.1 mol/L TEAA buffer solution for 3 times to obtain L-G-2-2.a.

The molar ration of the L-G-2-1, molecule skeleton containing carboxylic acid functional group, O-(7-azabenzotriazole-1-yl)-N,N,N',N'-trtramethyluronium hexafluorophosphate and N,N-ethyldiisopropylamine is 1:(1~2):(1~2):(2~4); the weight volume ratio of the described L-G-2-1 and halohydrocarbone derivative solvent is 1:(9~20) g/mL;

12. Adding $R^1$ ($R^1$ is synthetic building block, selected from isocyanate, benzyl alcohol or benzoic acid, i=1, 2 or 3), N,N-ethyldiisopropylamine and halohydrocarbon derived solvents into L-G-2-2.a; allowing reaction with stirring for 12-16 hours at 25° C.~30° C.; filtrating the solution to remove the solvent and obtaining a filtrated cake; washing the filtrated cake respectively with distilled water and 0.1 mol/L TEAA buffer solution for 3 times to obtain L-G-2-2-1.a;

the DNA encoded technology, disclosed by file application number: CN201210555548.3, nameed "Synthesis and Screening Method and Kit for A Lead Compound", is adopted after the purification process of each step for reactions of Synthetic Building Blocks, in order to perform bio-enzyme catalyzed DNA encoding on $R^1$, $R^2$ and $R^3$ in present invented compound library and to obtain L-G-3-1.a.

7. Removing CPG from the L-G-3-1.a by using alkaline removal method or light removal method to obtain DNA encoded compound library L-D-T-1.

Obviously, based on the above mentioned invention, different kinds of other modifications, substitutions or changes can be made according to normal technological knowledge and common tool in the present field but are still within the technological idea of the present invention.

To give a further detailed description of the present invention, some embodiments are given below. However, these embodiments should not be understood as the limits of scope that the present invention covers. Any technological solution based on the described content above lies in the scope of the present invention.

DETAILED DESCRIPTION

The raw materials and equipments used in the present invention are known products and can be purchased in the market.

Some abbreviations are given:

Fmoc: fluorenylmethoxycarbonyl group;

DMF: N,N-dimethylformamide;

DMSO: dimethyl sulfoxide;

DMT-MM: 2-chloro-4,6-dimethoxy-1,3,5-triazine;

TEAA: triethylammonium acetate; and

DETA: ethyldiisopropylamine.

Embodiment 1

(1). The Preparation of L-G-1

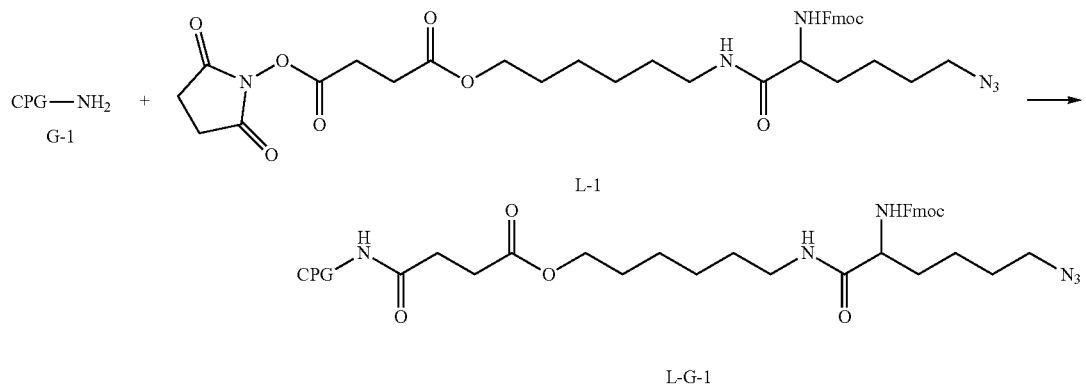

adding 3 mL of dichloromethane solution of compound L-1 (69 mg, 0.1 mmol, manufacturer: Aldrich) to G-1 (0.5 g, starting loading of CPG: 32 μmol/g, derived from Shanghai Lingjiang Industrial Development Co., Ltd) and allowing reaction overnight under room temperature; removing the solvent by filtration after the reaction to obtain a solid; washing the solid respectively with DMF (2 mL×3) and dichloromethane (2 mL×3) to obtain L-G-1.

Taking L-G-1, removing Fmoc protection group with piperidine, and determining that the loading of L-G-1 is 14.5 mol/g by measuring UV absorption of the Fmoc-removed product, the productivity is 91%.

(2) The Preparation of L-2

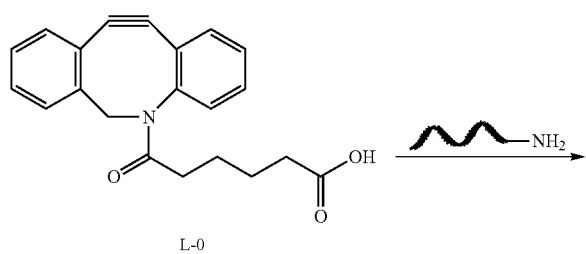

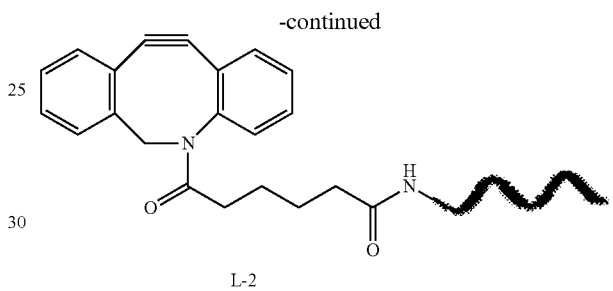

dissolving single strand DNA (32.0 nmol, molar weight is 7663.9) (sequence of the single strand DNA is GGAGCT-TGTGAATTCTGGCACTCG) into 30 μL NaHCO$_3$ buffer solution, adding successively 20 mL DMSO solution of L-0 (1.0 mg, 3.0 μmol, manufacturer: Aldrich) and 10 μL water solution of DMT-MM solution (0.83 mg, 3.0 μmol); allowing reaction overnight under room temperature; adjust pH to 4~5 with 3 mol/L HCl solution after the above mentioned reaction is finished; adding 240 μL ethanol and precipitating at −20° C. for 2 hours, and centrifugating to obtain a solid; washing the solid with 85% ethanol to obtain L-2, and determining that the amount of substance of L-2 is 28.0 nmol using OD ultraviolet absorption, the productivity is 80%.

MS(ESI) m/z 7979.6 (M+1)$^+$.

(3) The Preparation of L-G-2

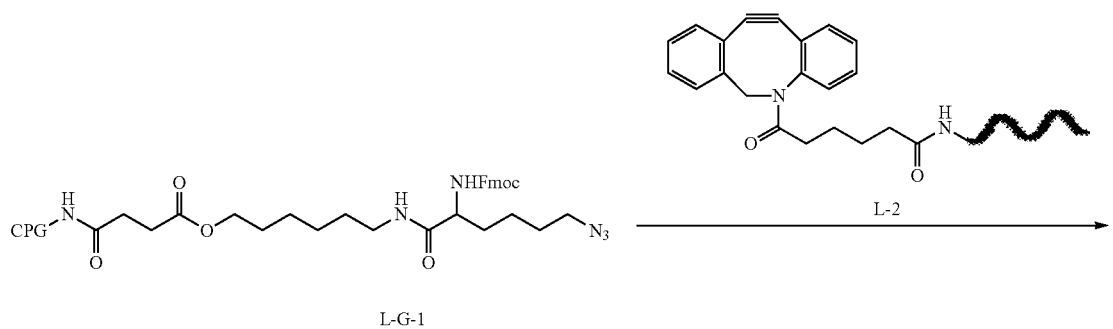

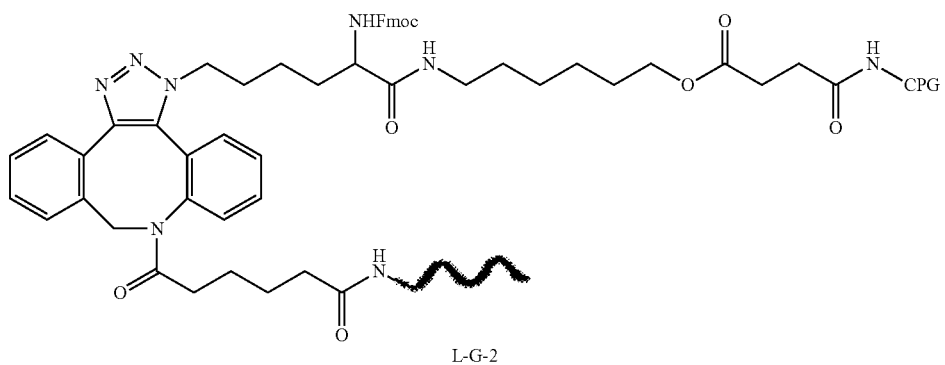

L-G-2 adding 90 μL aqueous solution of L-2 (28 nmol) and 10 μL pyridine into L-G-1 (10 mg, 140 nmol), and allowing reaction with stirring for 21 hours at 40° C.; filtrating the solution after the above mentioned reaction, removing the solvent to obtain a solid; washing the solid respectively with distilled water and 0.1 mol/L TEAA buffer solution for 3 times to obtain L-G-2.

(4) The Preparation of L-G-2-1

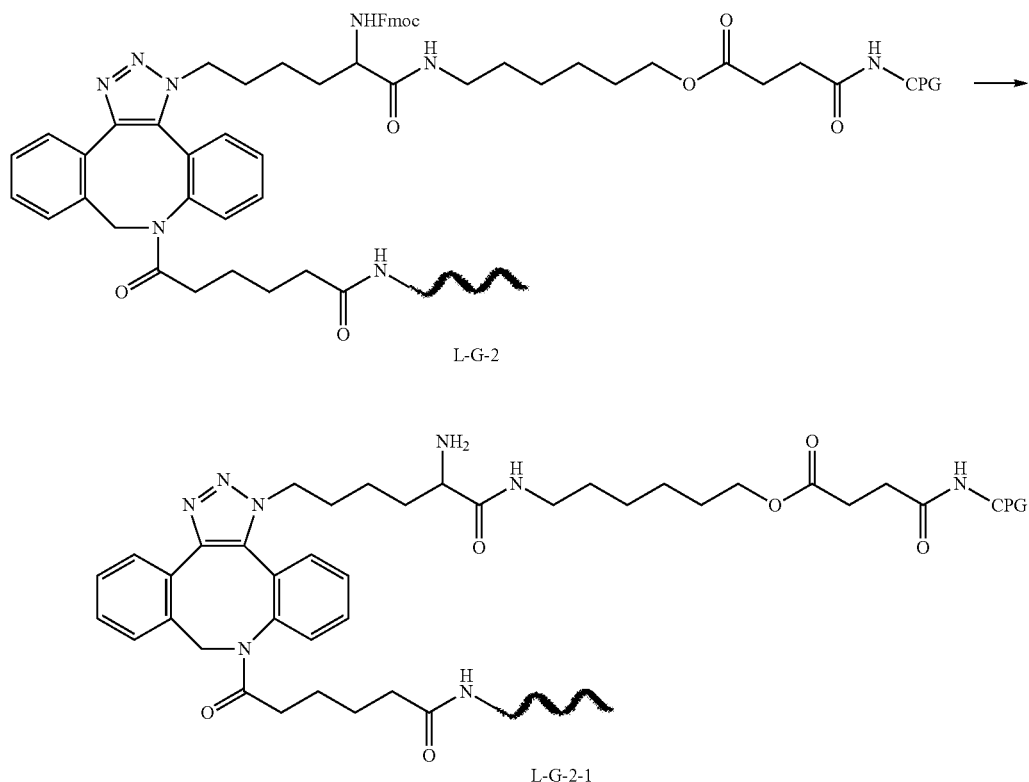

Adding DMF (160 μL) and pyridine (40 μL) into L-G-2 (8.0 mg), and allowing react with stirring for 6 hours at 25° C.~30° C.; filtrating the solution and removing the solvent to obtain a filtrated cake; washing the filtrated cake respectively with distilled water and 0.1 mol/L TEAA buffer solution for 3 times to obtain L-G-2-1.

Taking part of L-G-2-1 (3.0 mg), adding 150 μL of strong aqueous ammonia, and heating the solution to 55° C. and reacting for 1 hour to remove the solid carrier, removing the solvent by reducing the pressure after filtration process, washing the solid respectively with distilled water and 0.1 mol/L TEAA buffer solution for 3 times, adding 250 μL ethanol and 100 μL acetic acid-sodium acetate buffer solution (pH=4.7, 0.5 mol/L) to the solid and precipitating at −20° C. to obtain the DNA in L-G-2-1, determining that the amount of substance of DNA in L-G-2-1 is 6.0 nmol by using OD ultraviolet absorption, the productivity is 65%.

MS(ESI) m/z 8251.0 (M+1)$^+$.

(5) The Preparation of L-G-2-2.a

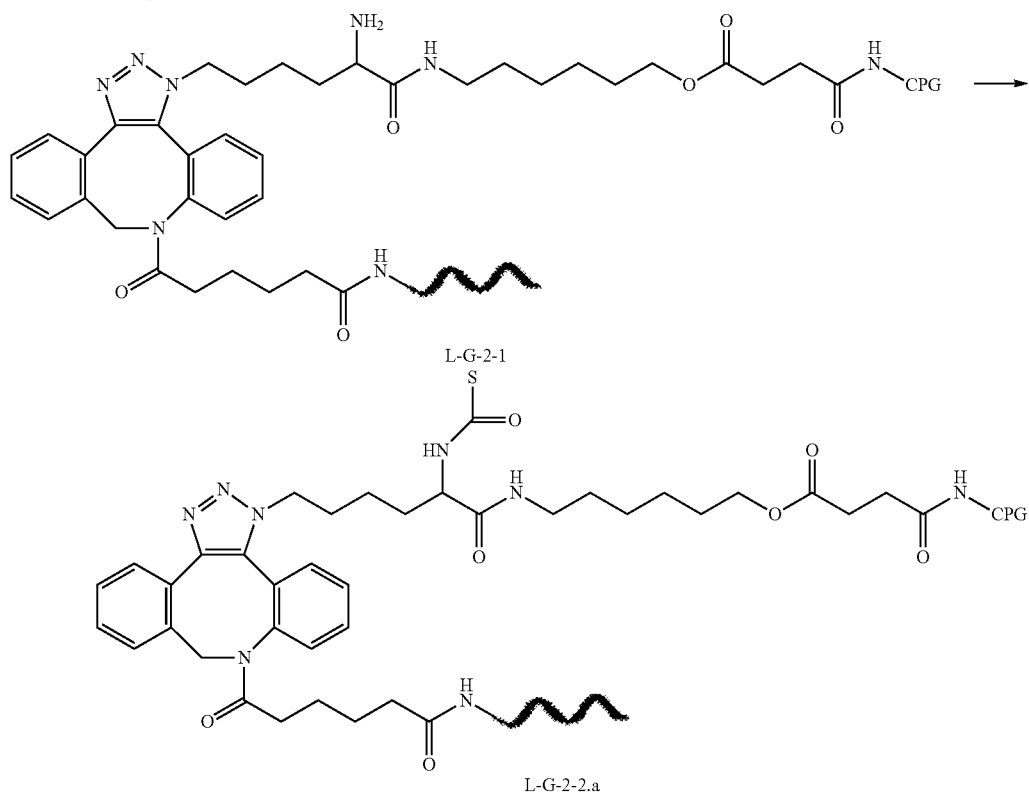

Adding molecule skeleton containing carboxylic acid, O-(7-azabenzotriazole-1-yl)-N,N,N',N'-trtramethyluronium hexafluorophosphate, DIEA as well as DMF into L-G-2-1 and allowing react with stirring for 16 hours at 25° C.~30° C.; filtrating the solution and removing the solvent to obtain a filtrated cake; washing the filtrated cake respectively with distilled water and 0.1 mol/L TEAA buffer solution for 3 times to obtain L-G-2-2.a.

More specifically,

Adding 4-aminobenzoic acid (4.15 mg, manufacturer: Alfa) O-(7-azabenzotriazole-1-yl)-N,N,N',N'-trtramethyluronium hexafluorophosphate (6.9 mg manufacturer: Alfa), DIEA (20 μL) as well as DMF (60 μL) into L-G-2-1 (20 mg) and allowing reaction with stirring for 12~16 hours at 25° C.~30° C.; filtrating the solution and removing the solvent to obtain a filtrated cake; washing the filtrated cake respectively with distilled water and 0.1 mol/L TEAA buffer solution for 3 times to obtain L-G-2-2.a.

Taking part of L-G-2-2.a (3.0 mg), adding 150 μL of strong aqueous ammonia and heating the solution to 55° C. for 1 hour to remove the solid carrier, removing the solvent by reducing the pressure after filtration process, washing respectively with distilled water and 0.1 mol/L TEAA buffer solution for 3 times. Adding 250 μL ethanol and 100 μL acetic acid-sodium acetate buffer solution (pH=4.7, 0.5 mol/L) to the solid and precipitating at −20° C. to obtain the DNA in L-G-2-2, determining that the amount of substance of DNA in L-G-2-1 is 4.5 nmol by using OD ultraviolet absorption, the productivity is 75%.

MS(ESI) m/z 8369.7 (M+1)+.

(6) The Preparation of L-G-3-1.a

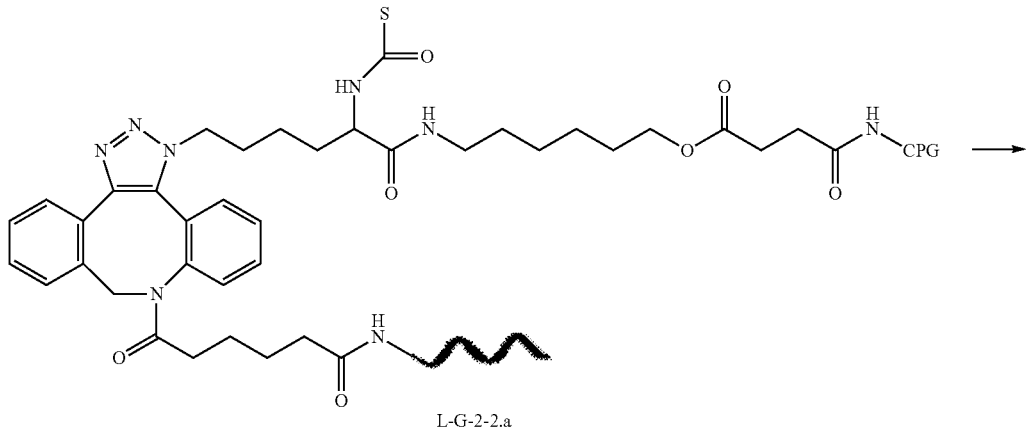

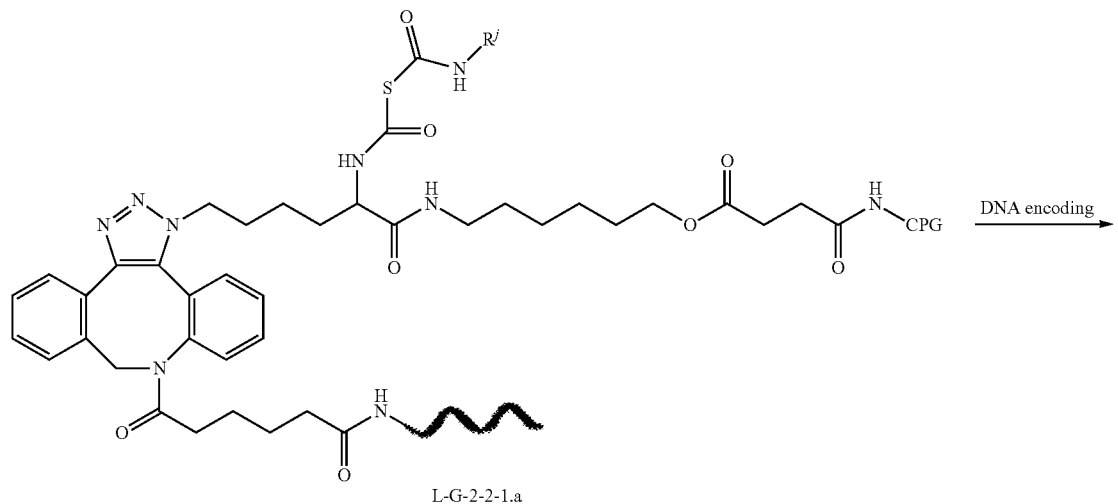

L-G-2-2-1.a → DNA encoding

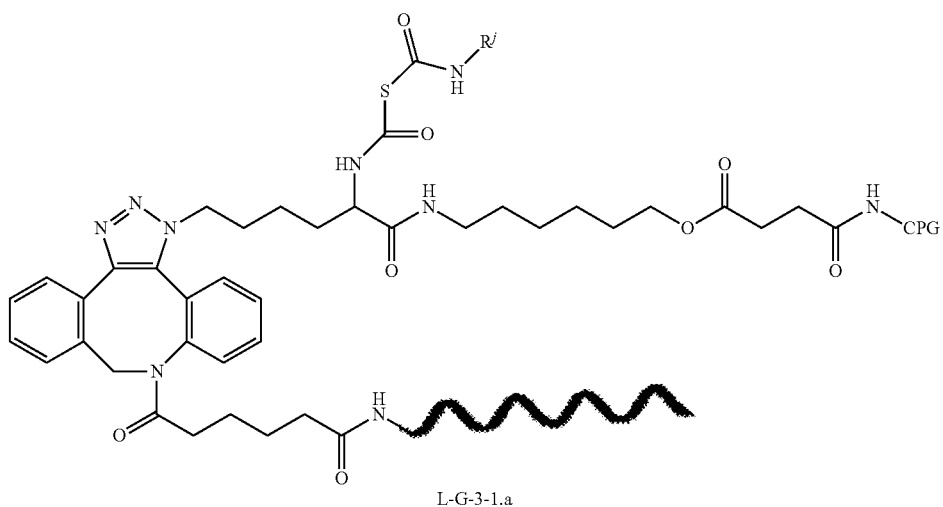

L-G-3-1.a adding $R^{j'}$ ($R^{j'}$ is synthetic building block and selected from substituted isocyanate), DIEA and DMF into L-G-2-2.a; allowing reaction with stirring for 16 hours at 25° C.~30° C.; filtrating the solution and removing the solvent to obtain a filtrated cake; washing the filtrated cake respectively with distilled water and 0.1 mol/L TEAA buffer solution for 3 times to obtain L-G-2-2-1.a;

referencing to the DNA encoded method disclosed in the patent named "Synthesis and Screening Method and Kit for Lead Compound" (application number: CN201210555548.3), L-G-2-1-1.a is performed DNA encoding in solid-phase condition (single strand DNA sequence is GGAGCTTGTGAAATCTGGCACTCG) to obtain L-G-3-1.a;

after the encoding, washing the solid respectively with 0.1 mol/L TEAA buffer solution (4×100 μL) and distilled water (4×100 μL), finally washing with 100 μL distilled water; taking a part of the solid washing, adding 50 μL of strong aqueous ammonia, and allowing reaction for 1 hour at 55° C.; washing the solid with 0.1 mol/L TEAA buffer solution and distilled water for 3 times; precipitating the filtrated solution by ethanol, and freeze-drying for agarose electrophoresis test.

(7) The Synthesis of Compound Library L-D-T-1

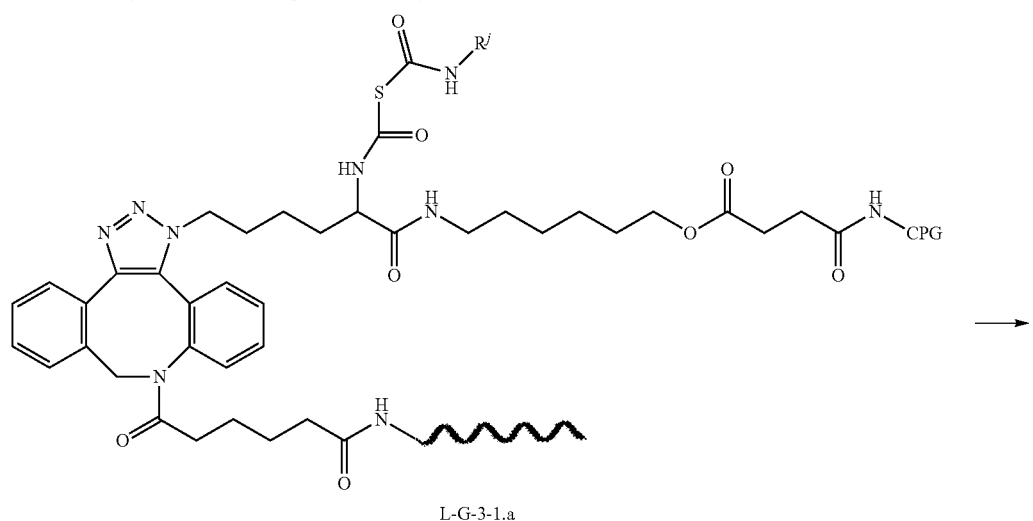

L-G-3-1.a

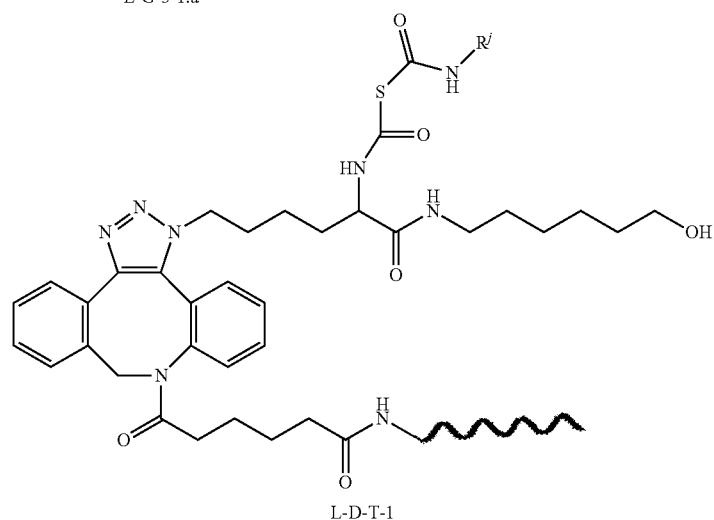

L-D-T-1 removing CPG from L-G-3-1.a by alkaline removal method or light removal method to obtain the DNA encoded compound library L-D-T-1.

Embodiment 2

(1) L-G-1 is obtained according to the preparation method for L-G-1 in embodiment 1;

(2) L-2 is obtained according to the preparation method for L-2 in embodiment 1;

(3) L-G-2 is obtained according to the preparation method for L-G-2 in embodiment 1;

(4) L-G-2-1 is obtained according to the preparation method for L-G-2-1 in embodiment 1; and (5) The Preparation of L-G-3-1.b

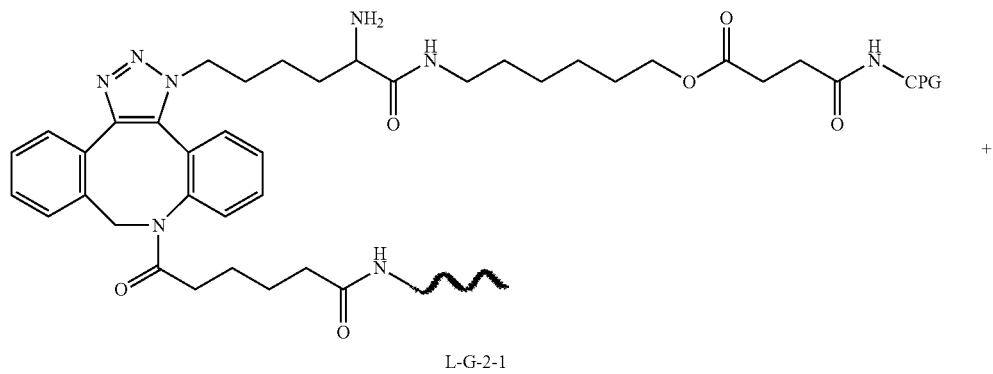

L-G-2-1

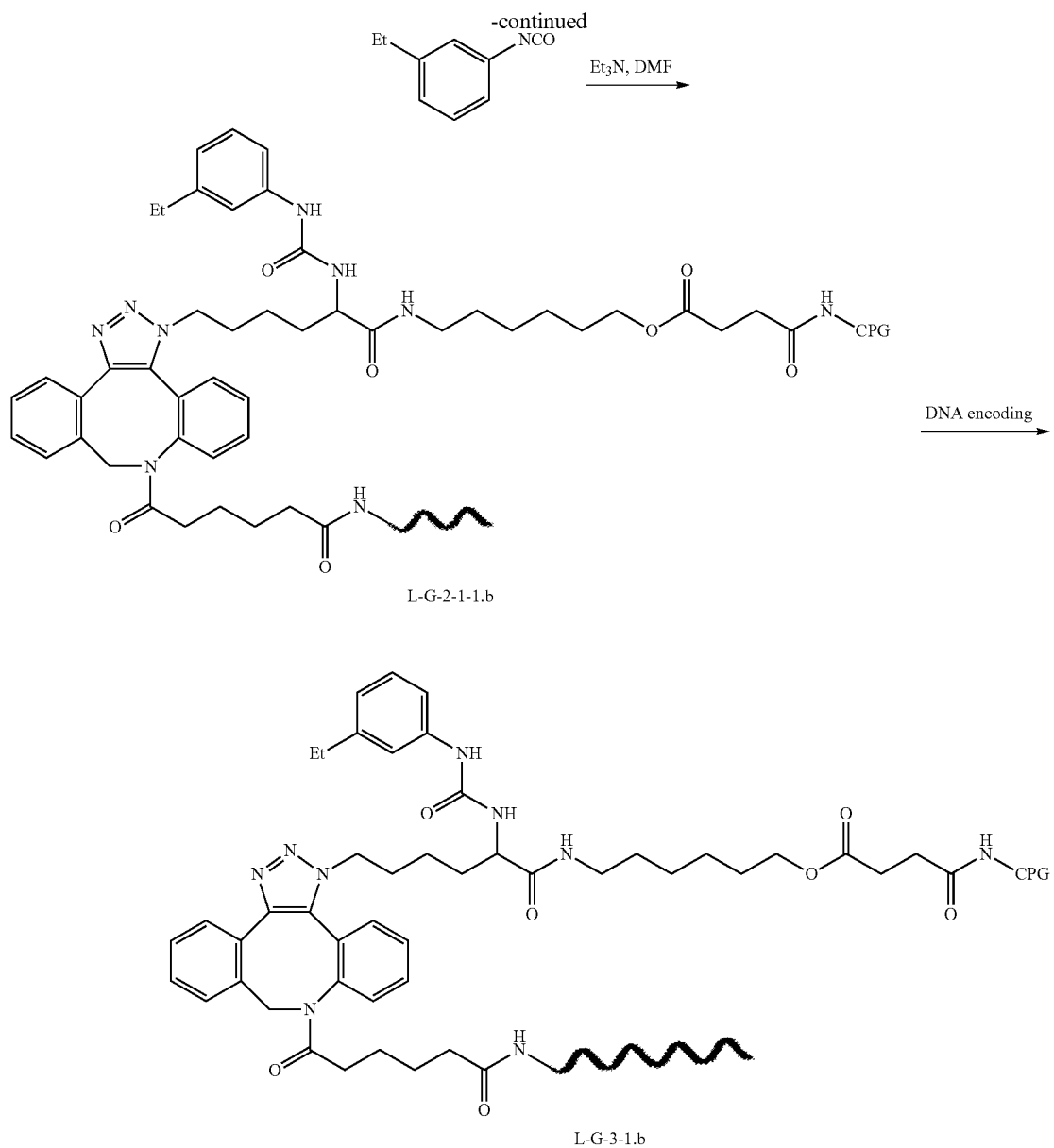

L-G-2-1-1.b

L-G-3-1.b adding 2-ethylphenyl isocyanate (1.47 mg, manufacturer: Alfa), triethylamine (5 μL) as well as DMF (15 μL) into L-G-2-1 (5 mg) and reacting for 16 hours at 25° C.~30° C.; filtrating the solution and removing the solvent to obtain a filtrated cake; washing the filtrated cake respectively with distilled water and 0.1 mol/L TEAA buffer solution for 3 times to obtain L-G-2-1-1.b;

taking part of L-G-2-1-1.b (2.0 mg), adding 150 μL of strong aqueous ammonia, and heating the solution to 55° C. for 1 hour to remove the solid carrier. Removing the solvent by reducing the pressure after filtration process, washing respectively with distilled water and 0.1 mol/L TEAA buffer solution for 3 times. Adding 250 μL ethanol and 100 μL acetic acid-sodium acetate buffer solution (pH=4.7, 0.5 mol/L) to the solid, precipitating at −20° C. to obtain DNA in L-G-2-1-1.b. The amount of substance is 2.5 nmol by using OD ultraviolet absorption quantitation, the productivity is 63%.

MS(ESI) m/z 8395.4 (M+1)$^+$.

Referencing to the DNA encoded method disclosed in the patent named "Synthesis and Screening Method and Kit for Lead Compound" (application number: CN201210555548.3), L-G-2-1-1.b is performed DNA encoding in solid-phase condition (single strand DNA sequence is GGAGCTTGTGAAATCTGGCACTCG) to obtain L-G-3-1.b;

after the encoding, washing the solid respectively with 0.1 mol/L TEAA buffer solution (4×100 μL) and distilled water (4×100 μL), finally washing with 100 μL distilled water; taking a part of solids after the irrigation, adding 50 μL of strong aqueous ammonia, and reacting for 1 hour at 55° C.; washing the obtained solid with 0.1 mol/L TEAA buffer solution and distilled water for 3 times; precipitating the filtrated solution by ethanol, and freeze-drying for agarose electrophoresis test.

(6) L-D-T-2 is Obtained According to the Preparation Method in Embodiment 1.

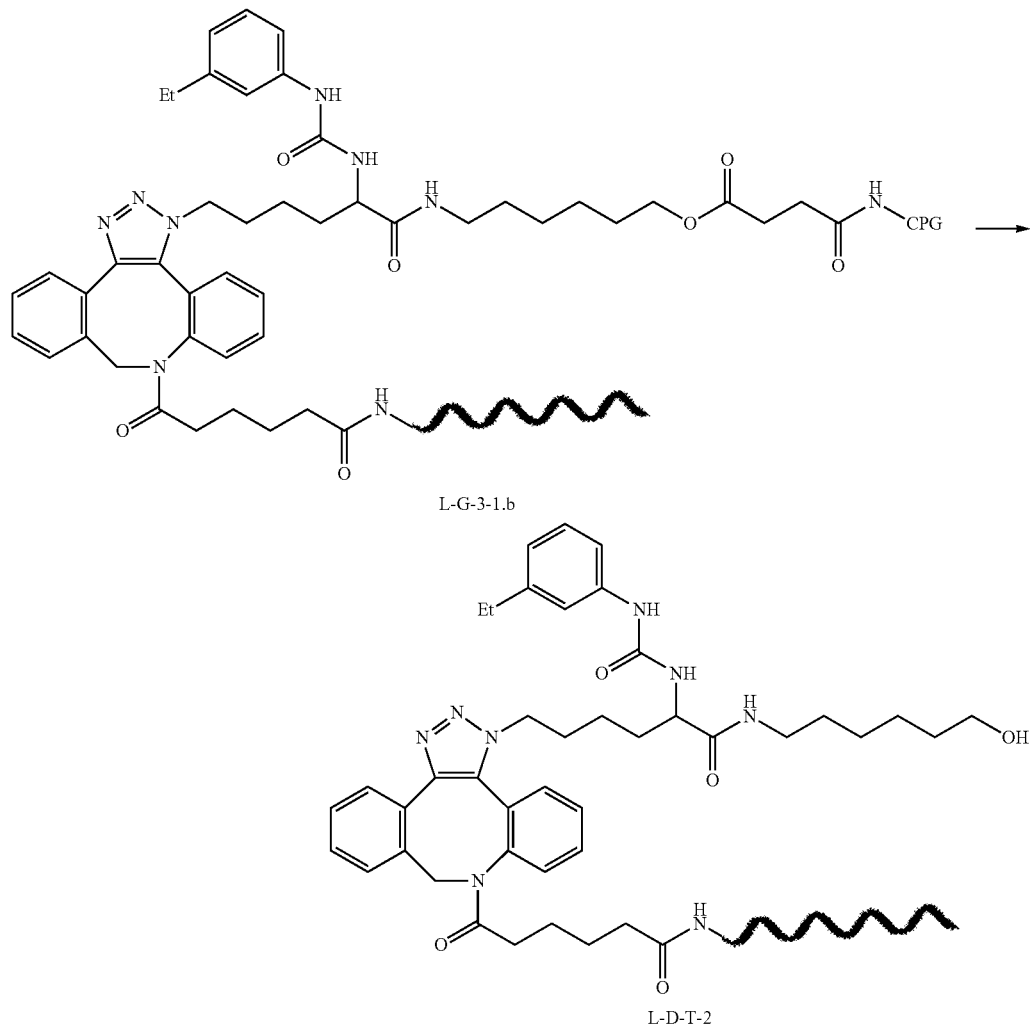

Embodiment 3

(1) L-G-1 is obtained according to the preparation method for L-G-1 in embodiment 1;
(2) L-2 is obtained according to the preparation method for L-2 in embodiment 1;
(3) L-G-2 is obtained according to the preparation method for L-G-2 in embodiment 1;
(4) L-G-2-1 is obtained according to the preparation method for L-G-2-1 in embodiment 1; and
(5) the preparation of L-G-2-2.c

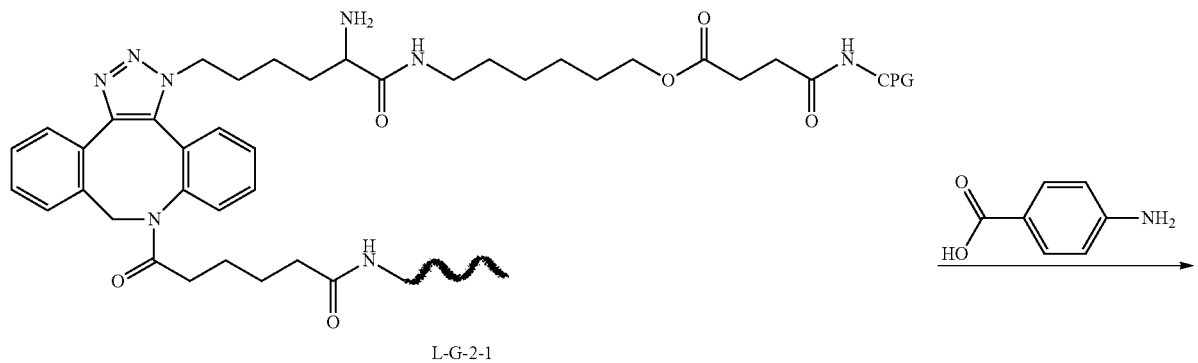

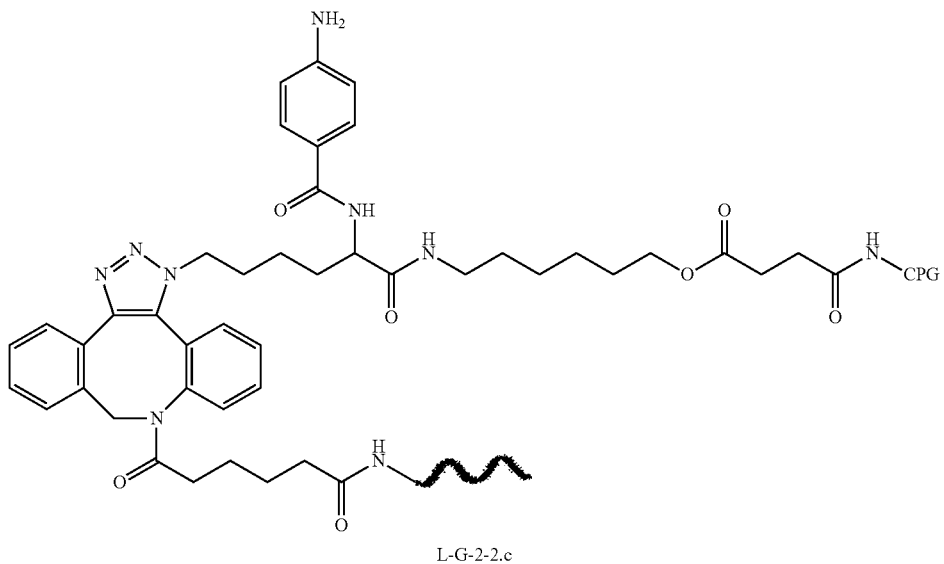

L-G-2-2.c adding 4-aminobenzoic acid (4.15 mg, manufacturer: Alfa), O-(7-azabenzotriazole-1-yl)-N,N,N',N'-trtramethyl-uronium hexafluorophosphate (6.9 mg, manufacturer: Alfa), DIEA (20 μL) as well as DMF (60 μL) into L-G-2-1 (20 mg), and reacting with stirring for 16 hours at 25° C.~30° C.; filtrating the solution to remove the solvent and to obtain a filtrated cake; washing the filtrated cake respectively with distilled water and 0.1 mol/L TEAA buffer solution for 3 times to obtain L-G-2-2.c;

taking part of L-G-2-2.c (2.0 mg), adding 150 μL of strong aqueous ammonia, and heating the solution to 55° C. for 1 hour to remove the solid carrier. Removing the solvent by reducing the pressure after filtration, washing the solid respectively with distilled water and 0.1 mol/L TEAA buffer solution for 3 times. Adding 250 μL ethanol and 100 μL acetic acid-sodium acetate buffer solution (pH=4.7, 0.5 mol/L) to the solid, precipitating at −20° C. to obtain DNA in L-G-2-2.c, the amount of substance of the obtained DNA in L-G-2-2.c is 3.0 nmol by using OD ultraviolet absorption quantification, the productivity is 75%.

MS(ESI) m/z 8369.7 (M+1)$^+$.

(6) The Preparation of L-G-3-1.c

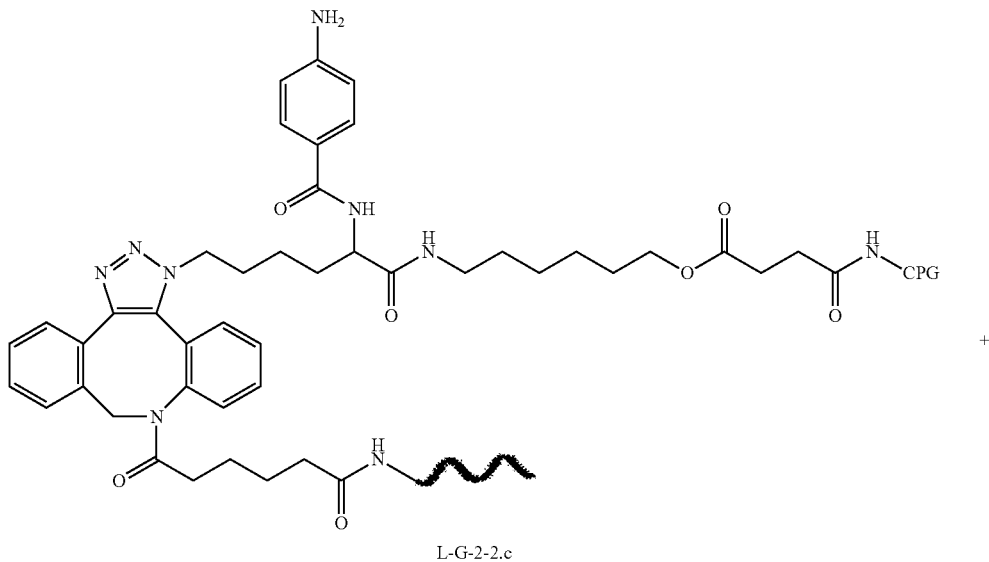

L-G-2-2.c

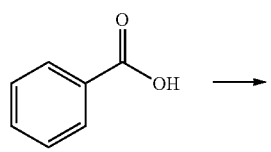

+

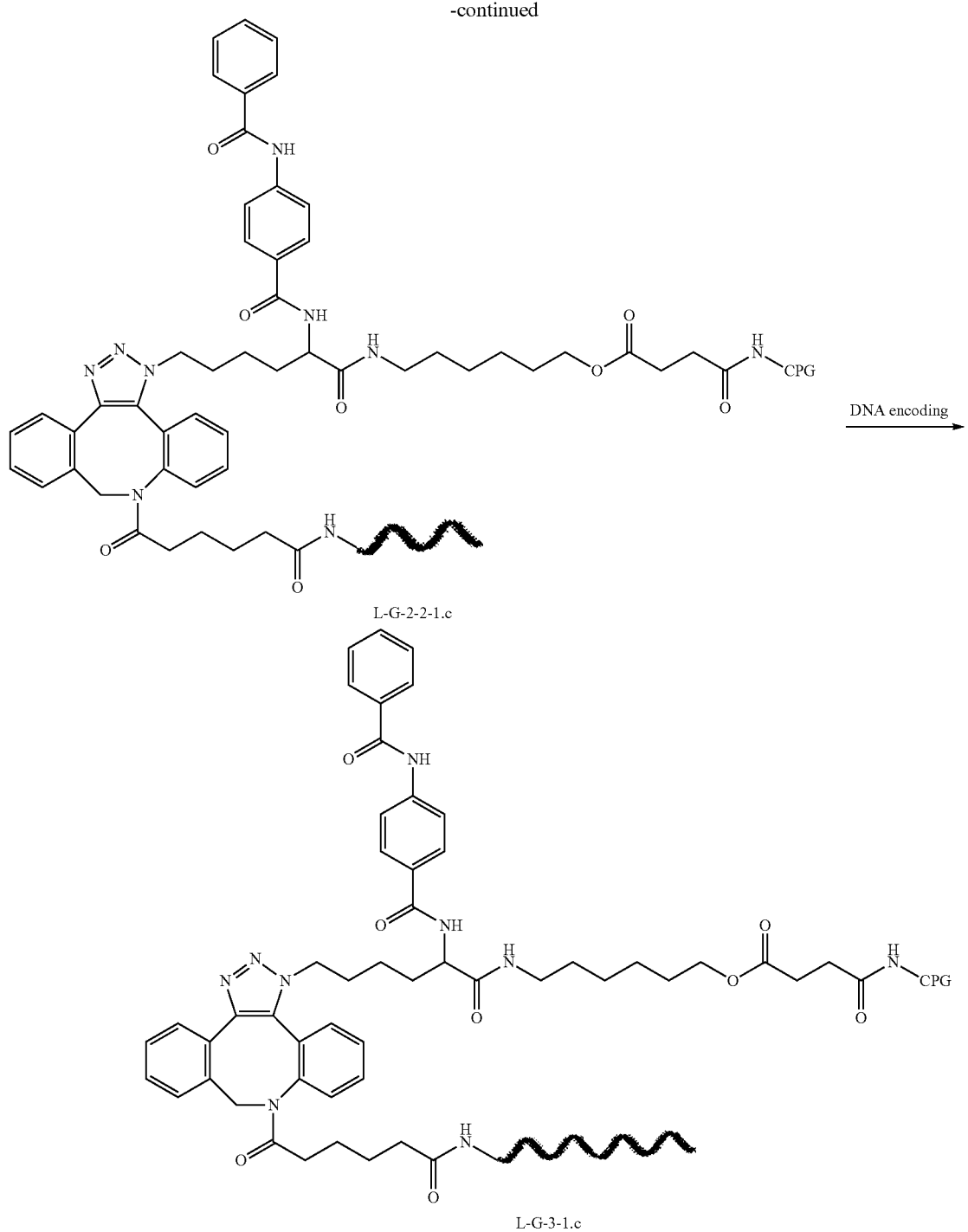

adding benzoic acid (2.0 mg), O-(7-azabenzotriazole-1-yl)-N,N,N',N'-trtramethyluronium hexafluorophosphate (6.9 mg, manufacturer: Alfa), DIEA (20 μL) as well as DMF (60 μL) into L-G-2-1 (20 mg), and reacting with stirring for 16 hours at 25° C.~30° C.; filtrating the solution to remove the solvent and obtaining a filtrated cake; washing the filtrated cake respectively with distilled water and 0.1 mol/L TEAA buffer solution for 3 times to obtain L-G-2-2-1.c;

taking part of L-G-2-2-1.c (2.0 mg), adding 150 μL of strong aqueous ammonia, and heating the solution to 55° C. for 1 hour to remove the solid carrier. Removing the solvent by reducing the pressure after filtration process, washing the solid respectively with distilled water and 0.1 mol/L TEAA buffer solution for 3 times. Adding 250 μL ethanol and 100 μL acetic acid-sodium acetate buffer solution (pH=4.7, 0.5 mol/L) to the solid, precipitating at −20° C. to obtain DNA in L-G-2-2-1.c, the amount of substance of the obtained DNA in L-G-2-2-1.c is 1.5 nmol by using OD ultraviolet absorption quantification, the productivity is 38%.

MS(ESI) m/z 8473.1 (M+1)$^+$.

Referencing to the DNA encoded method disclosed in the patent named "Synthesis and Screening Method and Kit for Lead Compound" (application number: CN201210555548.3), L-G-2-2-1.c is performed DNA encoding in solid-phase condition (single strand DNA sequence is GGAGCTTGTGAAATCTGGCACTCG) to obtain L-G-3-1.c;

after encoding, washing the solid respectively with 0.1 mol/L TEAA buffer solution (4×100 μL) and distilled water (4×100 μL), finally washing the solid with 100l L distilled water; taking a part of solid the irrigation, adding 50 μL of strong aqueous ammonia, and reacting for 1 hour at 55° C.; washing the obtained solid with 0.1 mol/L TEAA buffer solution and distilled water for 3 times; precipitating the filtrated solution by ethanol, and freeze-drying for agarose electrophoresis test.

(7) L-D-T-3 is Obtained According to the Preparation Method of L-D-T-1 in Embodiment 1.

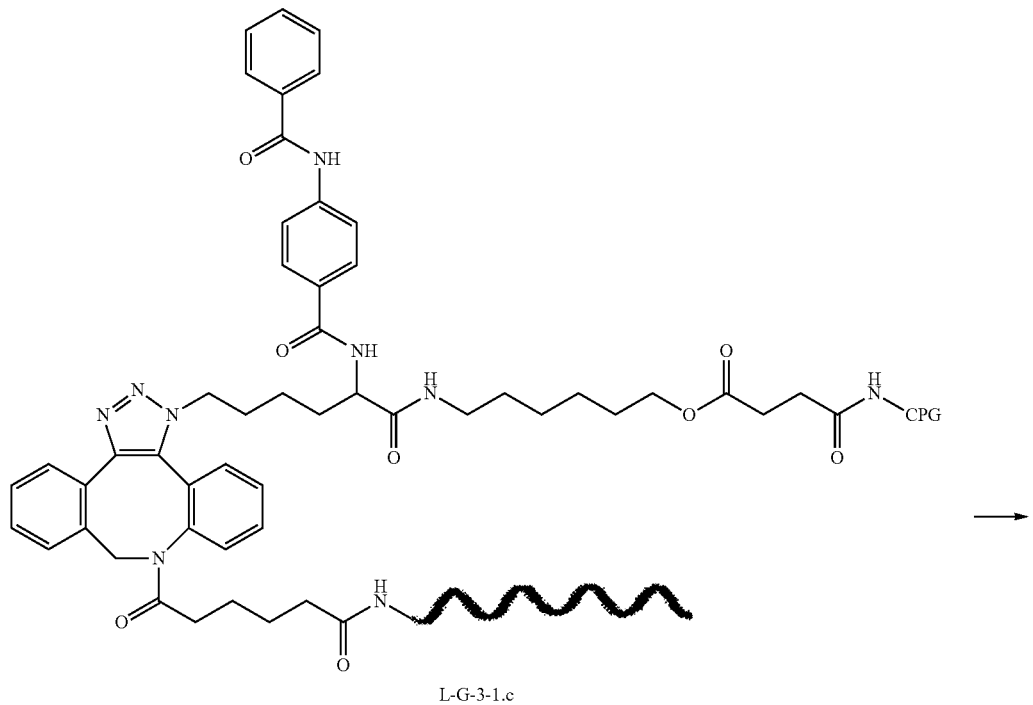

L-G-3-1.c

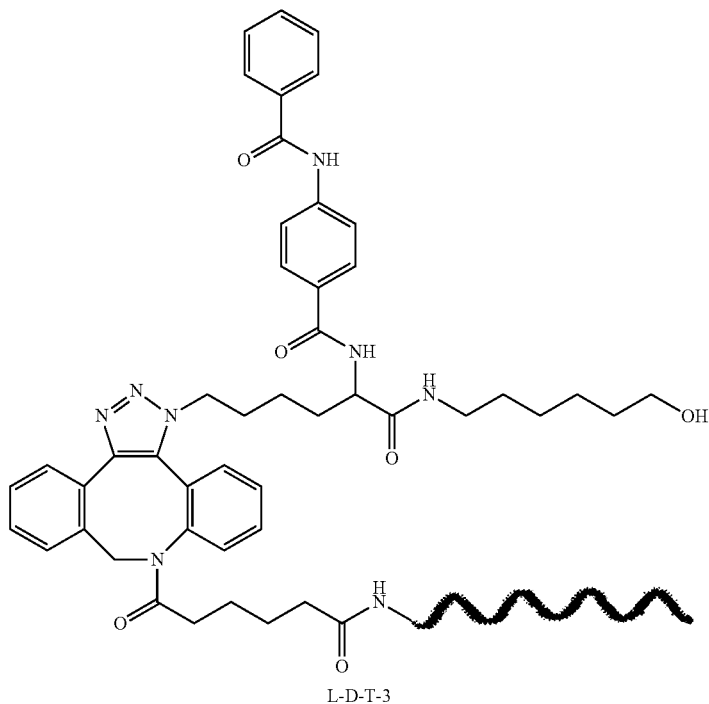

L-D-T-3

Embodiment 4

(1) L-G-1 is obtained according to the preparation method for L-G-1 in embodiment 1;
(2) L-2 is obtained according to the preparation method for L-2 in embodiment 1;
(3) L-G-2 is obtained according to the preparation method for L-G-2 in embodiment 1;
(4) L-G-2-1 is obtained according to the preparation method for L-G-2-1 in embodiment 1; and
(5) the preparation of L-G-2-2.d to remove the solvent and obtaining a filtrated cake; washing the filtrated cake respectively with distilled water and 0.1 mol/L TEAA buffer solution for 3 times to obtain L-G-2-2.d;

taking part of L-G-2-2.d (2.0 mg), adding 150 μL of strong aqueous ammonia, and heating the solution to 55° C. for 1 hour to remove the solid carrier. Removing the solvent by reducing the pressure after filtration process, washing the solid respectively with distilled water and 0.1 mol/L TEAA buffer solution for 3 times. Adding 250 μL ethanol and 100 μL acetic acid-sodium acetate buffer solution (pH=4.7, 0.5

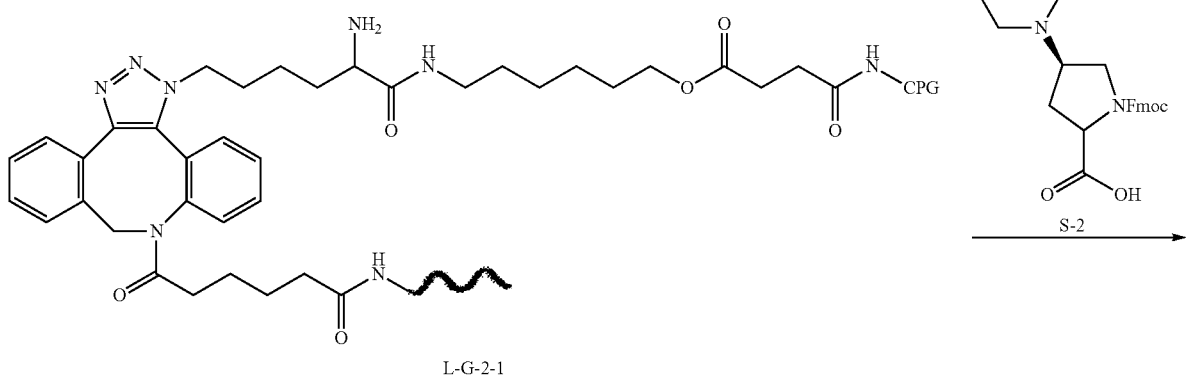

L-G-2-1

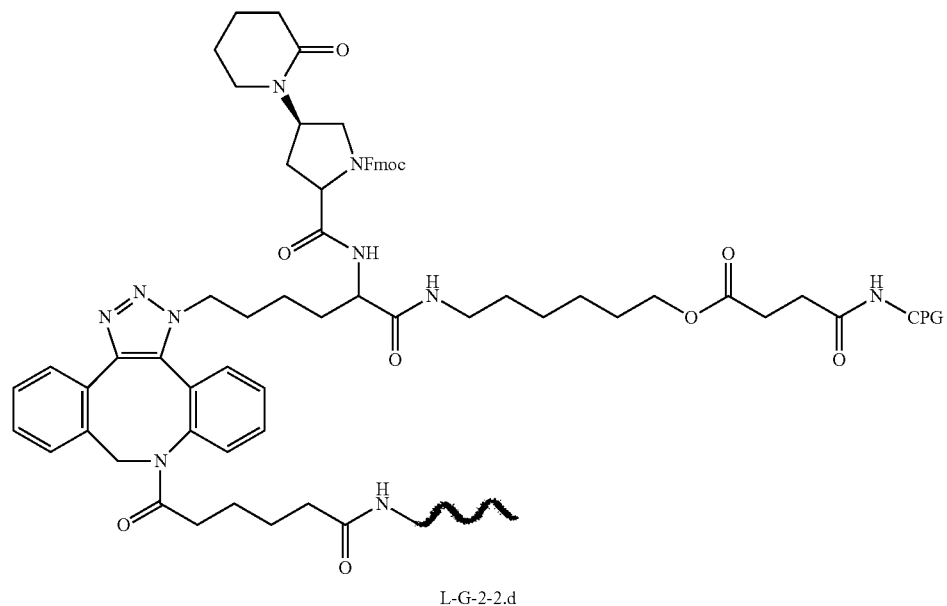

L-G-2-2.d adding S-2 (17.4 mg, manufacturer: Alfa), O-(7-azabenzotriazole-1-yl)-N, N,N',N'-trtramethyluronium hexafluorophosphate (6.9 mg, manufacturer: Alfa), DIEA (20 μL) as well as DMF (60 μL) into L-G-2-1 (20 mg) and reacting with stirring for 16 hours at 25° C.~30° C.; filtrating the solution mol/L) to the solid, precipitating at −20° C. to obtain DNA in L-G-2-2.d, the amount of substance of the obtained DNA in L-G-2-2.d is 2.0 nmol by using OD ultraviolet absorption quantification, the productivity is 50%.

MS(ESI) m/z 8698.0 $(M+1)^+$.

(6) The preparation of L-G-3-1.d

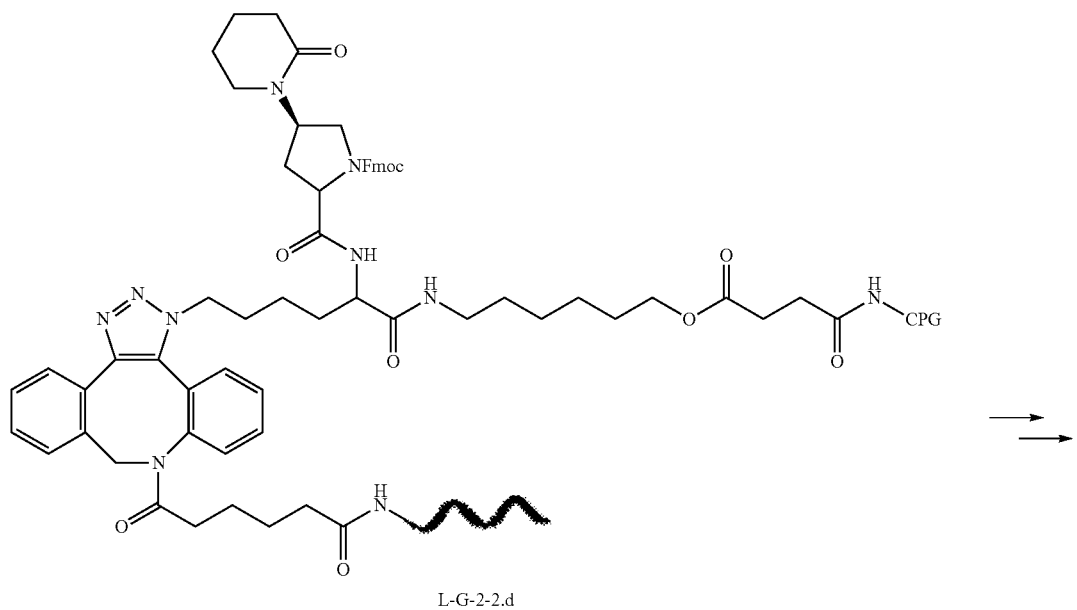

L-G-2-2.d

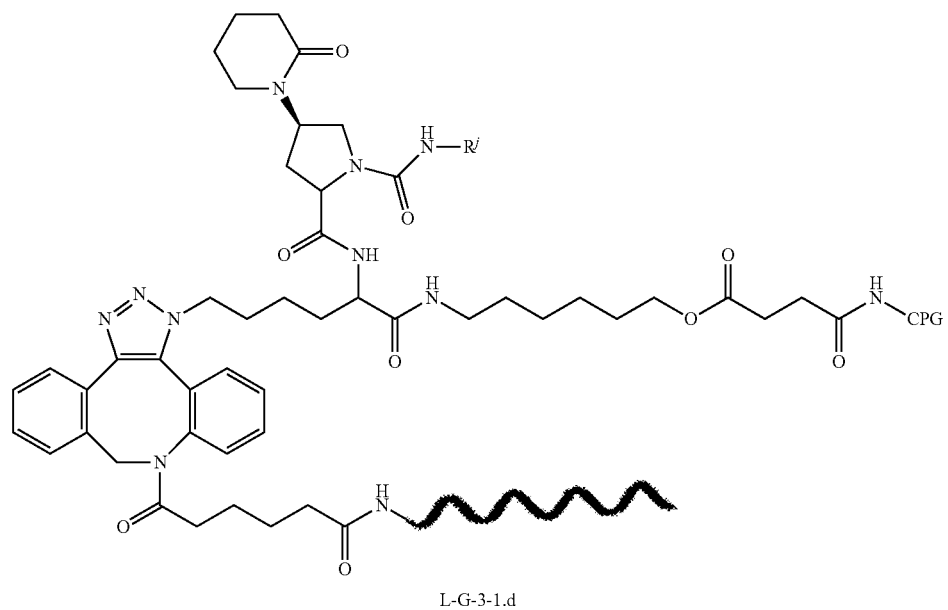

L-G-3-1.d adding piperidine (5 μL) into L-G-2-2.d (15 mg) and reacting with stirring for 6 hours at 25° C.~30° C.; filtrating the solution to remove the solvent and obtaining a filtrated cake; washing the filtrated cake respectively with distilled water and 0.1 mol/L TEAA buffer solution for 3 times to obtain a solid; adding R$^{j'}$ (R$^{j'}$ is selected from isocyanate substituted by RR, 1.5 mg), triethylamine (10 μL) as well as DMF (100 μL) into the solid; reacting with stirring for 16 hours at 25° C.~30° C.; filtrating the solution to remove the solvent and obtaining a filtrated cake; washing the filtrated cake respectively with distilled water and 0.1 mol/L TEAA buffer solution for 3 times to obtain L-G-2-2-1.d;

referencing to the DNA encoded method disclosed in the patent named "Synthesis and Screening Method and Kit for Lead Compound" (application number: CN201210555548.3), L-G-2-2-1.d is performed DNA encoding in solid-phase condition (single strand DNA sequence is GGAGCTTGTGAAATCTGGCACTCG) to obtain L-G-3-1.d;

after encoding, washing the solid respectively with 0.1 mol/L TEAA buffer solution (4*100 μL) and distilled water (4*100 μL), finally washing with 100 μL distilled water; taking a part of the solid after the irrigation, adding 50 μL of strong aqueous ammonia, and reacting for 1 hour at 55° C.; washing the obtained solid with 0.1 mol/L TEAA buffer solution and distilled water for 3 times; precipitating the filtrated solution by ethanol, and freeze-drying for agarose electrophoresis test.

(7) Synthesis of L-D-T-4 Compound Library

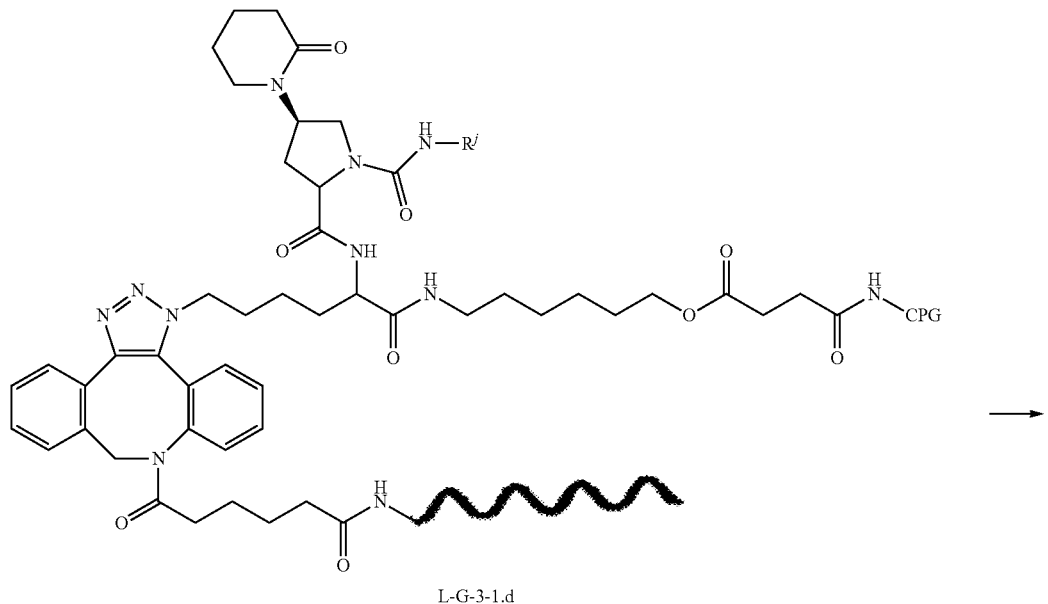

L-G-3-1.d

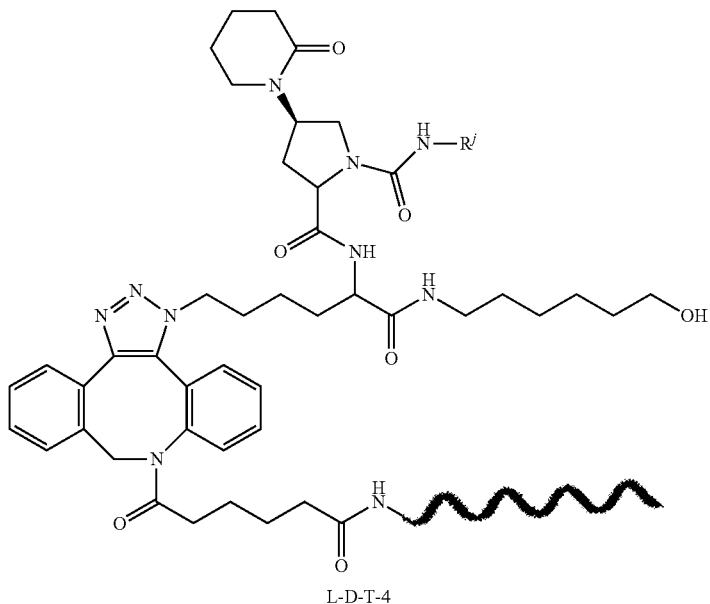

L-D-T-4 taking part of L-G-3-1.d (3.0 mg), adding 150 μL of strong aqueous ammonia, and heating the solution to 55° C. for 1 hour to remove the solid carrier. Removing the solvent by reducing the pressure after filtration process, washing the solid respectively with distilled water and 0.1 mol/L TEAA buffer solution for 3 times. Adding 250 μL ethanol and 100 μL acetic acid-sodium acetate buffer solution (pH=4.7, 0.5 mol/L) to the solid, and precipitating at −20° C. to obtain L-D-T-4.

Embodiment 5

(1) L-G-1 is obtained according to the preparation method for L-G-1 in embodiment 1;

(2) L-2 is obtained according to the preparation method for L-2 in embodiment 1;

(3) L-G-2 is obtained according to the preparation method for L-G-2 in embodiment 1;

(4) L-G-2-1 is obtained according to the preparation method for L-G-2-1 in embodiment 1; and (5) the preparation of L-G-2-2.e

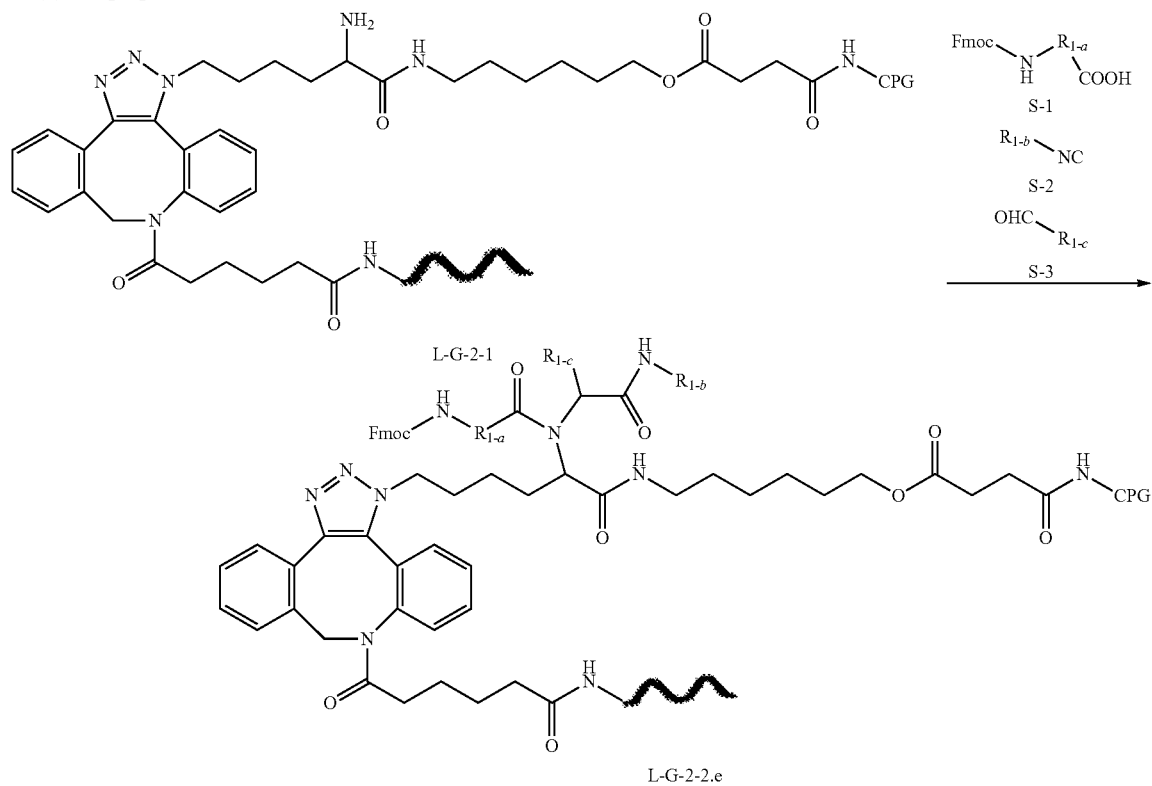

adding S-1, S-2 and S-3 as well as DMF into L-G-2-1 and reacting with stirring for 16 hours at 25° C.~30° C.; filtrating the solution to remove the solvent and obtaining a filtrated cake; washing the filtrated cake respectively with distilled water and 0.1 mol/L TEAA buffer solution for 3 times to obtain L-G-2-2.e.

Specifically, adding S-1 (FMOC-glycine, manufacturer: Alfa, 14.8 mg), S-2 (t-butylisocynide, manufacturer: Alfa, 4.2 mg) and S-3 (isovaleraldehyde, manufacturer: Alfa, 4.3 mg) as well as DMF (100 μL) into L-G-2-1 and reacting with stirring for 16 hours at 25° C.~30° C.; filtrating the solution to remove the solvent and obtaining a filtrated cake; washing the filtrated cake respectively with distilled water and 0.1 mol/L TEAA buffer solution for 3 times to obtain L-G-2-2.e;

taking part of L-G-2-2-1.e (2.0 mg), adding 150 μL of strong aqueous ammonia to, and heating the solution to 55° C. for 1 hour to remove the solid carrier. Removing the solvent by reducing the pressure after filtration process, finally washing the solid respectively with distilled water and 0.1 mol/L TEAA buffer solution for 3 times. Adding 250 μL ethanol and 100 μL acetic acid-sodium acetate buffer solution (pH=4.7, 0.5 mol/L) to the solid, precipitating at −20° C. to obtain DNA in L-G-2-2.e, the amount of substance of DNA in L-G-2-2.e is 38 nmol by using OD ultraviolet absorption quantitation, the productivity is 76%.

MS(ESI) m/z 9111.4 (M+1)$^+$.

(6) The preparation of L-G-3-1.e

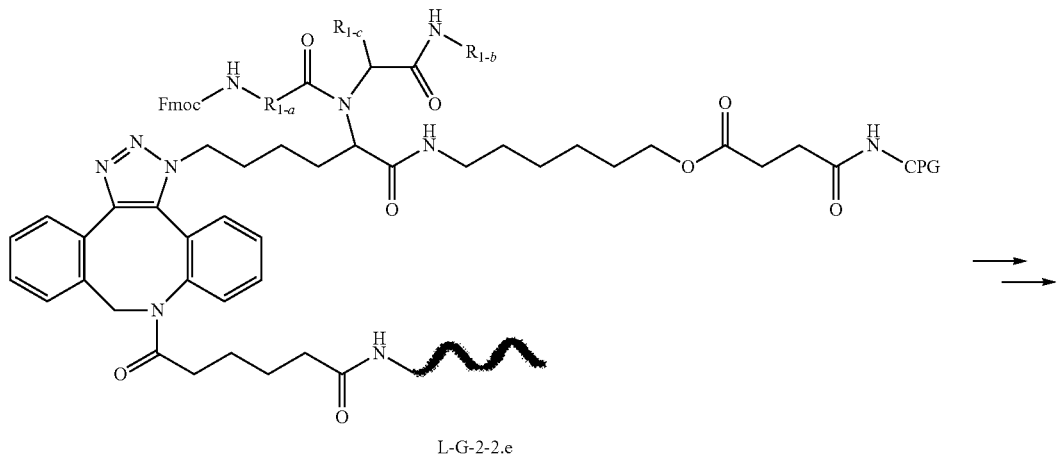

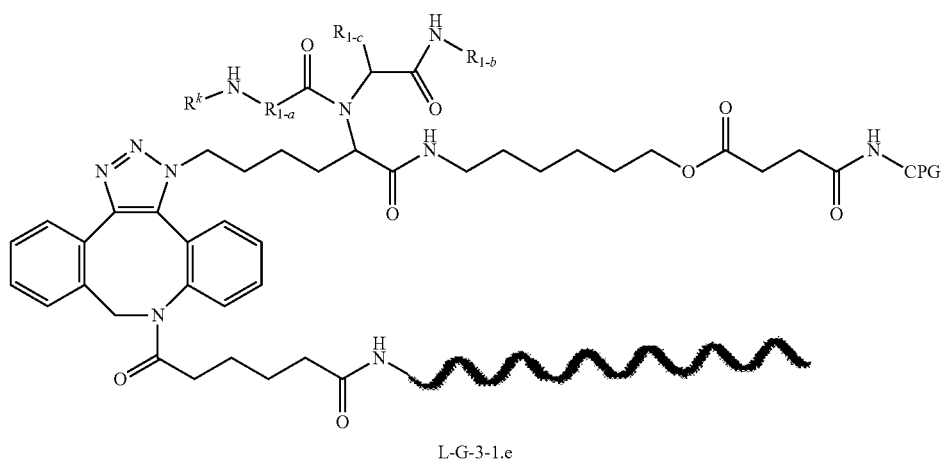

L-G-3-1.e referencing to the DNA encoded method disclosed in the patent named "Synthesis and Screening Method and Kit for Lead Compound" (application number: CN201210555548.3), L-G-2-2-1.e is performed DNA encoding in solid-phase condition (single strand DNA sequence is GGAGCTTGTGAAATCTGGCACTCG) to obtain L-G-3-1.e;

after encoding, washing the solid respectively with 0.1 mol/L TEAA buffer solution (4×100 μL) and distilled water (4×100 μL), finally washing with 100 μL distilled water; taking a part of the solid after the irrigation, adding 50 μL of strong aqueous ammonia, and reacting for 1 hour at 55° C.; washing the obtained solid with 0.1 mol/L TEAA buffer solution and distilled water for 3 times; precipitating the filtrated solution by ethanol, freeze-drying for agarose electrophoresis test;

adding piperidine (40 μL) into L-G-2-2-1.e (10 mg) and reacting with stirring for 6 hours at 25° C.~30° C.; filtrating the solution to remove the solvent and obtaining a filtrated cake; washing the filtrated cake respectively with distilled water and 0.1 mol/L TEAA buffer solution for 3 times to obtain a solid; adding $R^{k'}$ ($R^{k'}$ is selected from synthetic building block containing carboxylic acids, aldehydes or isocyanates), O-(7-azbenzotriazole-1-yl)-N,N,N',N'-tetramethyluronium hexafluorophosphate (6.1 mg, manufacturer: Alfa), DIEA (20 μL) as well as DMF (60 μL) into the solid; reacting with stirring for 16 hours at 25° C.~30° C.; filtrating the solution to remove the solvent and obtaining a filtrated cake; washing the filtrated cake respectively with distilled water and 0.1 mol/L TEAA buffer solution for 3 times to obtain L-G-3-1-1.e;

referencing to the DNA encoded method disclosed in the patent named "Synthesis and Screening Method and Kit for Lead Compound" (application number: CN201210555548.3), L-G-3-1-1.e is performed DNA encoding in solid-phase condition (single strand DNA sequence is GGAGCTTGTGAAATCTGGCACTCG) to obtain L-G-3-1.e; after encoding, washing the solid respectively with 0.1 mol/L TEAA buffer solution (4×100 μL) and distilled water (4×100 μL), finally washing with 100 μL distilled water; taking a part of the solid after the irrigation, adding 50 μL of strong aqueous ammonia, and reacting for 1 hour at 55° C.; washing the obtained solid with 0.1 mol/L TEAA buffer solution and distilled water for 3 times; precipitating the filtrated solution by ethanol, and freeze-drying for agarose electrophoresis test; and (7) Synthesis of L-D-T-5 Compound Library

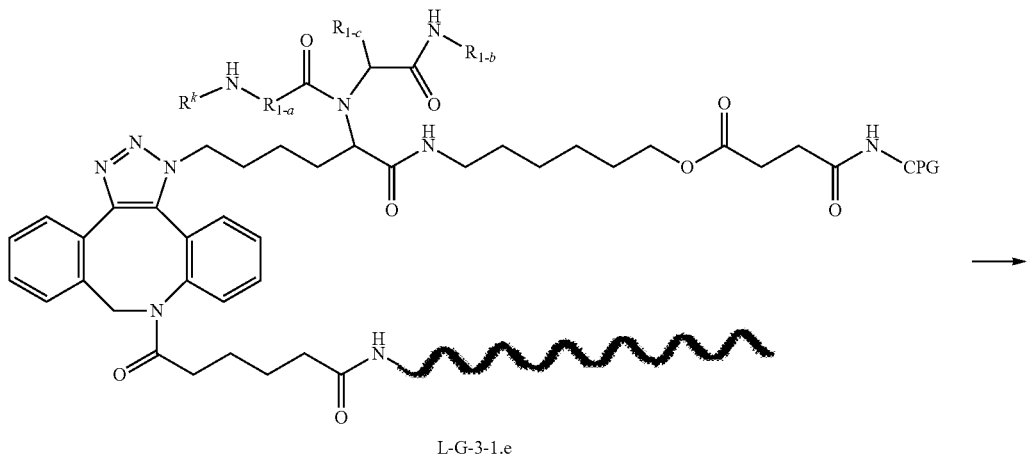

L-G-3-1.e

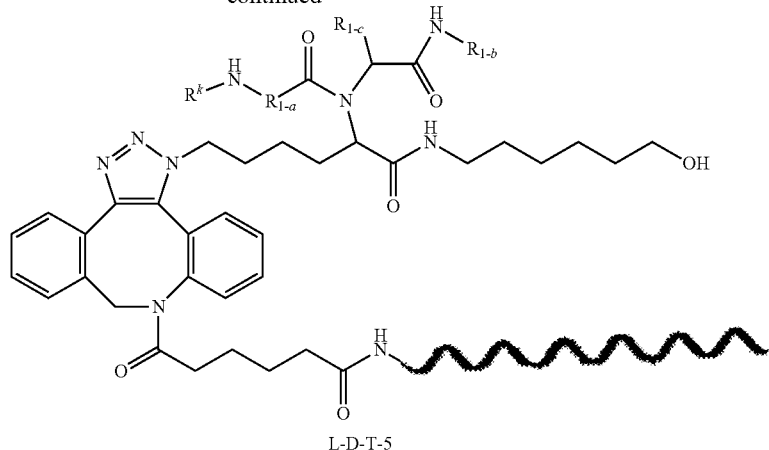

L-D-T-5 taking part of L-G-3-1.e (2.0 mg), adding 40 μL of aqueous ammonia, and heating the solution to 55° C. for 1 hour to remove the solid carrier. Washing the solid respectively with distilled water and 0.1 mol/L TEAA buffer solution for several times to obtain filtrated solution; concentrating the filtrated solution, and adding appropriate ethanol, precipitating at −20° C. and centrifugating to obtain a solid; washing the solid with 85% ethanol to obtain DNA encode compound library L-D-T-5 is finally.

Embodiment 6

(1) L-G-1 is obtained according to the preparation method for L-G-1 in embodiment 1;

(2) L-2 is obtained according to the preparation method for L-2 in embodiment 1;

(3) L-G-2 is obtained according to the preparation method for L-G-2 in embodiment 1;

(4) L-G-2-1 is obtained according to the preparation method for L-G-2-1 in embodiment 1; and (5) the preparation of L-G-2-2.f

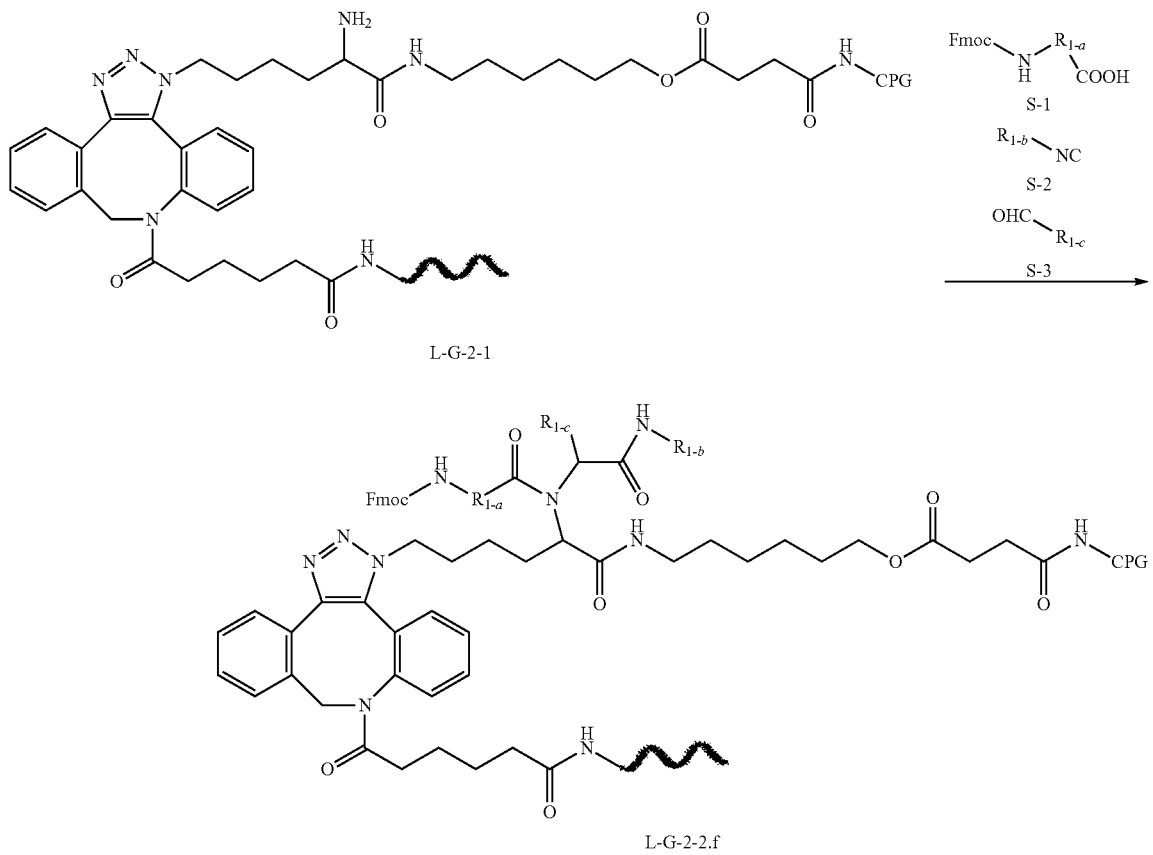

adding S-1, S-2 and S-3 as well as DMF into L-G-2-1, and reacting with stirring for 16 hours at 25° C. 30° C.; filtrating the solution to remove the solvent and obtaining a filtrated cake; washing the filtrated cake respectively with distilled water and 0.1 mol/L TEAA buffer solution for 3 times to obtain L-G-2-2.f.

Specifically, adding S-1 (FMOC-L-phenylalanine, manufacturer: Alfa, 15.1 mg), S-2 (cyclohexylisocynide, manufacturer: Alfa, 4.8 mg) and S-3 (cyclopentylaldehyde, manufacturer: Alfa, 4.1 mg) as well as DMF (100 μL) into L-G-2-1 (20 mg), and reacting with stirring for 16 hours at 25° C.~30° C.; filtrating the solution to remove the solvent and obtaining the filtrated cake; washing the filtrated cake respectively with distilled water and 0.1M TEAA buffer solution for 3 times to obtain L-G-2-2.f;

taking part of L-G-2-2-1.d (2.0 mg), adding 150 μL of strong aqueous ammonia, and heating the solution to 55° C. for 1 hour to remove the solid carrier. Removing the solvent by reducing the pressure after filtration process, washing the solid respectively with distilled water and 0.1 mol/L TEAA buffer solution for 3 times. Adding 250 μL ethanol and 100 μL acetic acid-sodium acetate buffer solution (pH=4.7, 0.5 mol/L) to the solid, precipitating at −20° C. to obtain DNA in L-G-2-2.f, the amount of substance of DNA in L-G-2-2.f is 35 nmol by using OD ultraviolet absorption quantitation, the productivity is 70%.

MS(ESI) m/z 9241.9 (M+1)$^+$.

(6) The Preparation of L-G-3-1.f referencing to the DNA encoded method disclosed in the patent named "Synthesis and Screening Method and Kit for Lead Compound" (application number: CN201210555548.3), L-G-2-2.f is performed DNA encoding in solid-phase condition (single strand DNA sequence is GGAGCTTGTGAAATCTGGCACTCG) to obtain L-G-2-2-1.f; after encoding, washing the solid respectively with 0.1 mol/L TEAA buffer solution (4×100 μL) and distilled water (4×100 μL), finally washing with 100 μL distilled water; taking part of the solid after washing, adding 50 μL of strong aqueous ammonia, and reacting for 1 hour at 55° C.; washing the obtained solid with 0.1 mol/L TEAA buffer solution and distilled water for 3 times; precipitating the filtrated solution by ethanol, and freeze-drying for agarose electrophoresis test;

taking part of L-G-2-2-1.f (10 mg), adding piperidine (40 μL), and reacting with stirring for 6 hours at 25° C.~30° C.; filtrating the solution to remove the solvent and obtaining a filtrated cake; washing the filtrated cake respectively with distilled water and 0.1 mol/L TEAA buffer solution for 3 times to obtain the solid; add $R^{k'}$ ($R^{k'}$ is selected from synthetic building block containing carboxylic acids, aldehydes or isocyanates), O-(7-azbenzotriazole-1-yl)-N,N,N', N'-tetramethyluronium hexafluorophosphate (6.1 mg, manufacturer: Alfa), DIEA (20 μL) as well as DMF (60 μL) into the solid; reacting with stirring for 16 hours at 25° C.~30° C.; filtrating the solution to remove the solvent and obtaining a filtrated cake; washing the filtrated cake respectively with distilled water and 0.1 mol/L TEAA buffer solution for 3 times to obtain L-G-3-1-1.f;

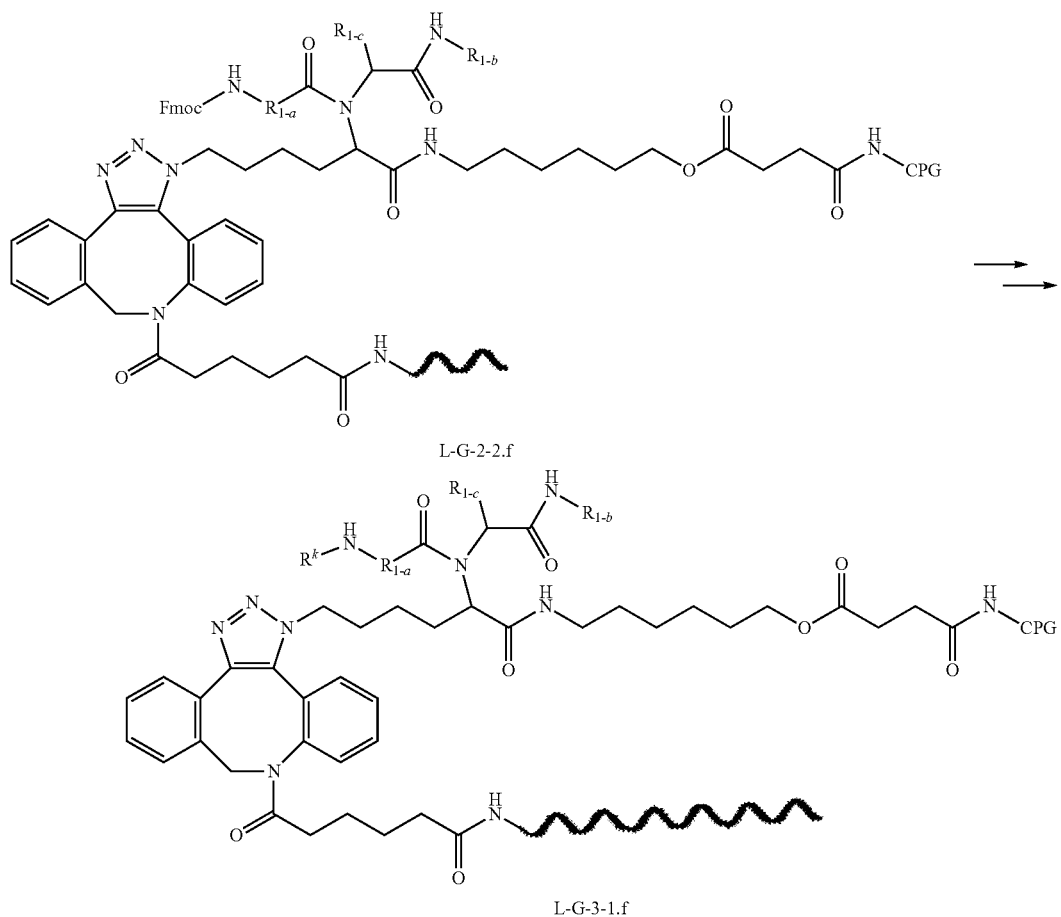

L-G-2-2.f

L-G-3-1.f referencing to the DNA encoded method disclosed in the patent named "Synthesis and Screening Method and Kit for Lead Compound" (application number: CN201210555548.3), L-G-3-1-1.f is performed DNA encoding in solid-phase condition (single strand DNA sequence is GGAGCTTGTGAAATCTGGCACTCG) to obtain L-G-3-1.f; after encoding, washing the solid respectively with 0.1 mol/L TEAA buffer solution (4×100 μL) and distilled water (4×100 μL), finally washing with 100 μL distilled water; taking part of the solid after washing, adding 50 μL of strong aqueous ammonia, and reacting for 1 hour at 55° C.; washing the obtained solid with 0.1 mol/L TEAA buffer solution and distilled water for 3 times; precipitating the filtrated solution by ethanol, freeze-drying for agarose electrophoresis test; and (7) Synthesis of L-D-T-6 Compound Library phase condition successfully reacted, and further enlarge reaction types of coding compound library and the space of diversity of the encoded compound library. The enlarged reaction types include organic catalyzed aldol reactions, alkenes metathesis reactions etc. In the traditional liquid phase DNA encoded compound library the efficiencies are rather low, while the present invention significantly increase the synthesis efficiencies of these reactions.

Compared with the existed method for liquid phase synthesis of DNA encoded compound library, the synthesis technology with CPG carrying DNA encoded compound in the present invention, performs the after-reaction purification process through several simple filtration and washing procedures. It simplifies the after-process of chemical synthesis and of DNA encode reactions, and simplifies the processes of separation and purification. It also shortens the

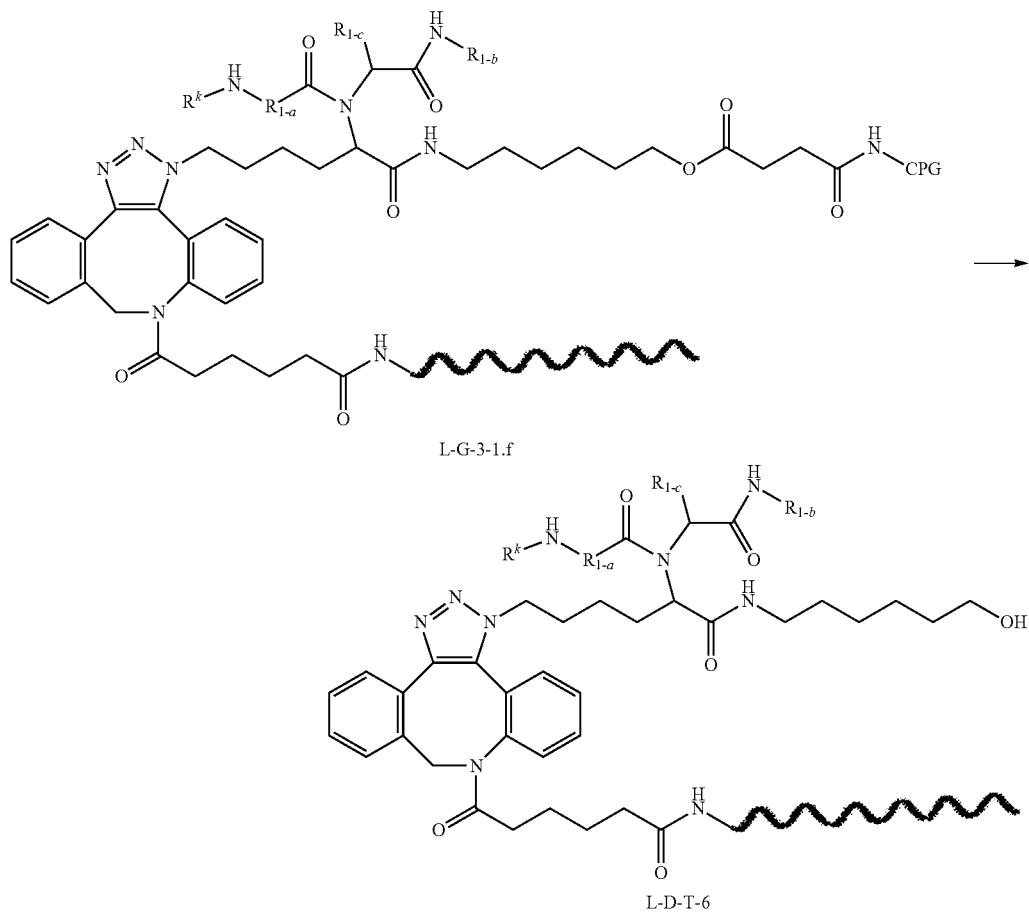

taking part of L-G-3-1.f (2.0 mg), adding 40 μL of aqueous ammonia, and heating the solution to 55° C. for 1 hour to remove the solid carrier. Washing the solid respectively with distilled water and 0.1 mol/L TEAA buffer solution for several times to obtain a filtrated solution; concentrating the filtrated solution, and adding appropriate amount of ethanol, precipitating at −20° C. and centrifugating to obtain a solid; washing the solid with 85% ethanol to obtain DNA encode compound library L-D-T-6.

The present invention can realize synthesis of DNA coding compound in organic solvent system. It can make the unrealized or relatively low synthesis of chemical reaction in the DNAcoding compound library in the traditional liquid cycle of synthesis of compound library at more than 50% and saves the cost enormously. Moreover, it significantly enhances the purified quality, that is, enhances the purity of final products and enhance the DNA encoding efficiency as well as unicity.

The method for synthesis of DNA encoded compound library in the present invention, is able to remove the excessive DNA, decreases the interference which excessive DNA would make on the following screening process during the DNA encoded compound library synthesis and also significantly increases the targeting ability and the accuracy on the screening of new pharmaceuticals.

The linker molecules in the present invention, connect the CPG, DNA and small molecules at a suitable distance. Thus the forces between molecules can be formed and also be broken under moderate condition, which makes a variety of reactions happens with the co-existence of DNA and CPG.

What is claimed is:

1. A method for solid-phase synthesis of a DNA-encoded compound library, comprising:

(a) reacting controlled pore glass (CPG) beads comprising a free amine as a solid carrier with a first linker

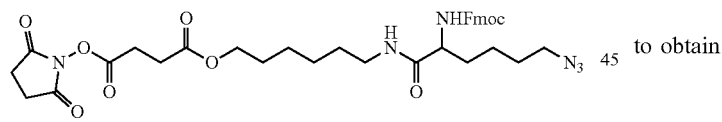

in an organic solvent to obtain

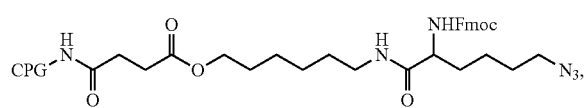

wherein the resulting product is filtrated to remove the organic solvent and then washed by an organic solvent; and Fmoc is a protecting group fluorenylmethoxycarbonyl;

(b) reacting a single-stranded DNA (ssDNA) with a second linker

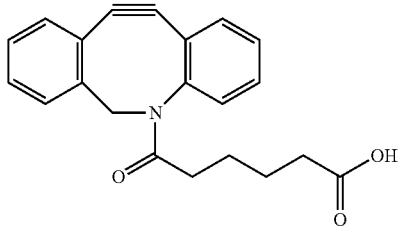 [SMILES: O=C(O)CCCCC(=O)N1Cc2ccccc2C#Cc2ccccc21]

to obtain

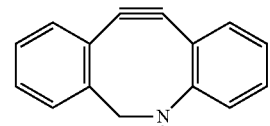

wherein the resulting product is precipitated, washed with ethanol, and centrifuged;

(c) reacting

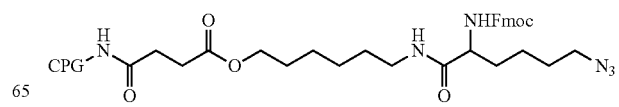

with

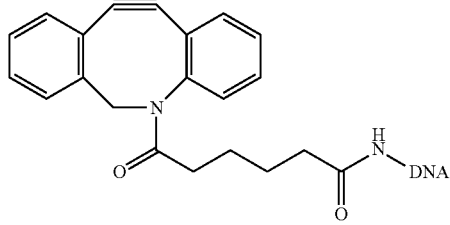

in an organic solvent to obtain

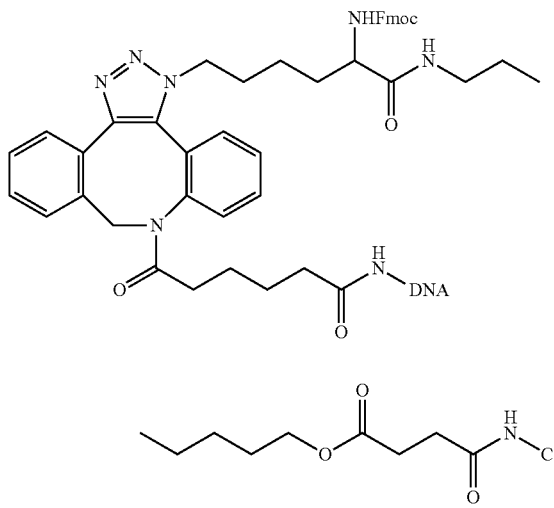

wherein the resulting product is filtrated to remove the solvent and then washed with water and a triethylammonium acetate (TEAA) buffer solution;

(d) removing the Fmoc protecting group by contact with a base to obtain

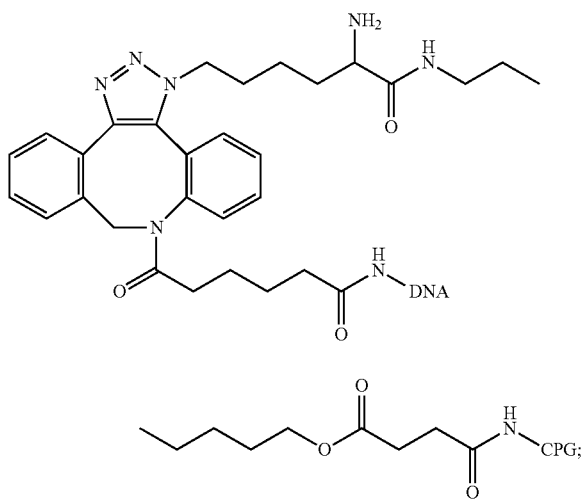

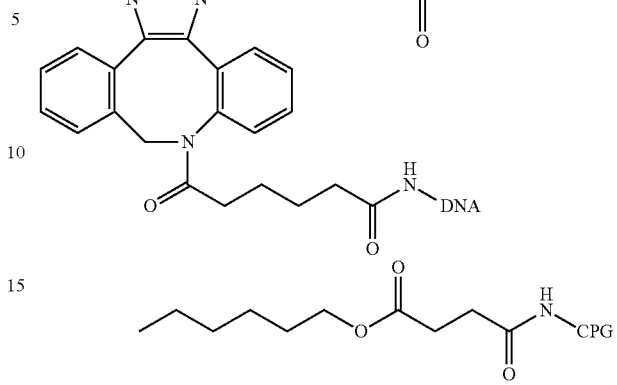

(e) reacting with a skeleton molecule comprising a carboxylic acid which reacts with the free amine of the first linker, in an organic solvent, wherein the skeleton molecule is selected from the group consisting of 4-aminobenzoic acid, dl-4-hydroxyphenylglycine, Fmoc-glycine, Fmoc-1-phenylalanine, t-butylisocynide, cyclohexyl isocyanide, 3-methyl butyraldehyde, cyclopentyl aldehyde and

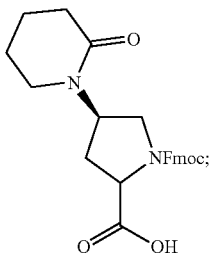

(f) reacting the product obtained in step (e) with a synthetic building block, wherein the synthetic building block is selected from the group consisting of isocyanate, benzyl alcohol and benzoic acid;

(g) perform DNA-encoding on the product obtained in step (f), wherein the synthetic building block is specifically labeled by a marker sequence which is connected to the ssDNA; and (h) cleaving the product obtained in step (g) from the solid carrier to obtain a DNA-encoded compound library.

2. The method of claim 1, wherein in step (a), the organic solvent for reaction is dichloromethane.

3. The method of claim 1, wherein the product obtained in step (a) is washed by DMF and dichloromethane.

4. The method of claim 1, wherein in step (d), the base is pyridine.

5. The method of claim 1, wherein the ssDNA has the sequence of GGAGCTTGTGAATTCTGGCACTCG.

6. The method of claim 1, further comprising: before step (f), performing DNA-encoding on the product obtained in (e), wherein the skeleton molecule is specifically labeled by a marker sequence which is connected to the ssDNA.

7. The method of claim 1, wherein in step (h), the step of cleaving the product obtained in step (g) from the solid carrier is carried out in ammonium hydroxide.

8. The method of claim 1, wherein in step (e), the skeleton molecule is 4-aminobenzoic acid.

9. The method of claim 8, wherein the product obtained in step (e) is
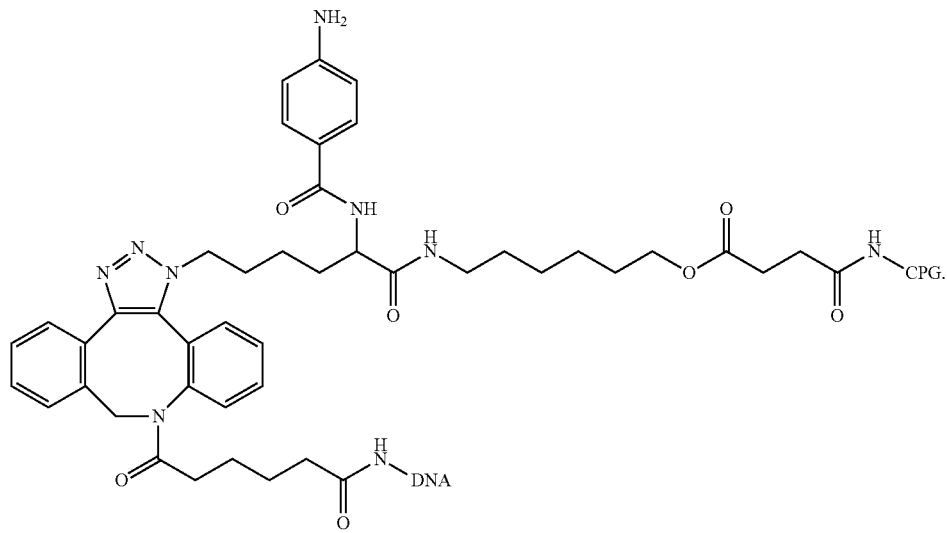
10. The method of claim 1, wherein in step (e), the skeleton molecule is
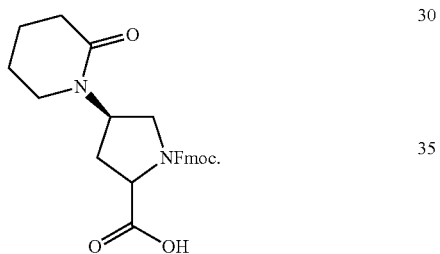
11. The method of claim 10, wherein the product obtained in step (e) is
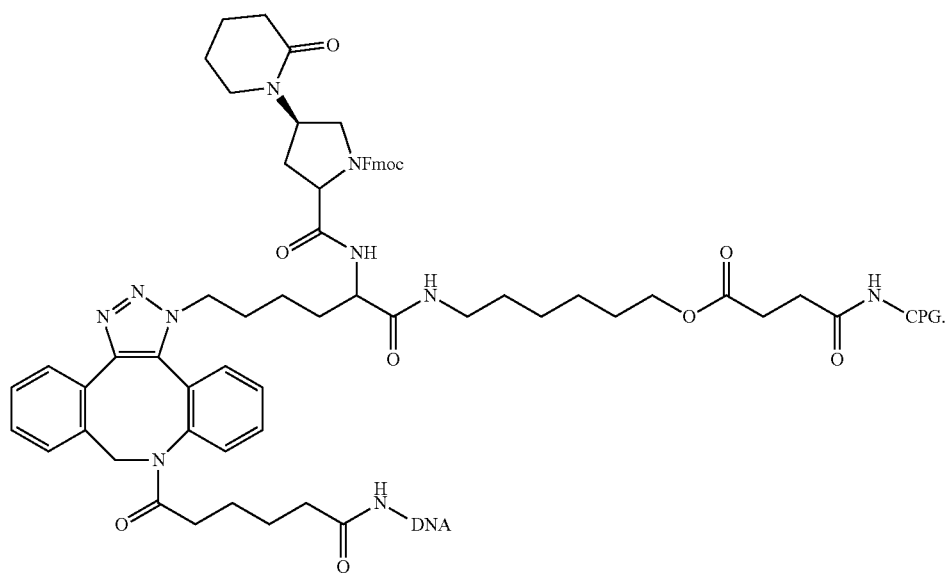

12. The method of claim 1, wherein in step (e), the skeleton molecule is a combination of Fmoc-glycine, t-butylisocynide and 3-methyl butyraldehyde.

13. The method of claim 1, wherein in step (e), the skeleton molecule is a combination of Fmoc-1-phenylalanine, cyclohexyl isocyanide and cyclopentyl aldehyde.

14. The method of claim 1, wherein in step (f), the synthetic building block is isocyanate.

15. The method of claim 1, herein in step (f), the synthetic building block is benzoic acid.

* * * * *

```
                              SEQUENCE LISTING

<160> NUMBER OF SEQ ID NOS: 9

<210> SEQ ID NO 1
<211> LENGTH: 24
<212> TYPE: DNA
<213> ORGANISM: Artificial Sequence
<220> FEATURE:
<223> OTHER INFORMATION: synthetic

<400> SEQUENCE: 1
ggagcttgtg aattctggca ctcg                                          24

<210> SEQ ID NO 2
<211> LENGTH: 24
<212> TYPE: DNA
<213> ORGANISM: Artificial Sequence
<220> FEATURE:
<223> OTHER INFORMATION: synthetic

<400> SEQUENCE: 2
ggagcttgtg aattctggca ctcg                                          24

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggagcttgtg aattctggca ctcg                                          24

<210> SEQ ID NO 4
<211> LENGTH: 24
<212> TYPE: DNA
<213> ORGANISM: Artificial Sequence
<220> FEATURE:
<223> OTHER INFORMATION: synthetic

<400> SEQUENCE: 4
ggagcttgtg aattctggca ctcg                                          24

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
ggagcttgtg aattctggca ctcg                                          24

<210> SEQ ID NO 6
<211> LENGTH: 24
<212> TYPE: DNA
<213> ORGANISM: Artificial Sequence
<220> FEATURE:
<223> OTHER INFORMATION: synthetic

<400> SEQUENCE: 6
ggagcttgtg aattctggca ctcg                                          24
```

```
<210> SEQ ID NO 7
<211> LENGTH: 24
<212> TYPE: DNA
<213> ORGANISM: Artificial Sequence
<220> FEATURE:
<223> OTHER INFORMATION: synthetic

<400> SEQUENCE: 7
ggagcttgtg aattctggca ctcg                                         24

<210> SEQ ID NO 8
<211> LENGTH: 24
<212> TYPE: DNA
<213> ORGANISM: Artificial Sequence
<220> FEATURE:
<223> OTHER INFORMATION: synthetic

<400> SEQUENCE: 8
ggagcttgtg aattctggca ctcg                                         24

<210> SEQ ID NO 9
<211> LENGTH: 24
<212> TYPE: DNA
<213> ORGANISM: Artificial Sequence
<220> FEATURE:
<223> OTHER INFORMATION: synthetic

<400> SEQUENCE: 9
ggagcttgtg aattctggca ctcg                                         24
```